US010030238B2

(12) United States Patent
Cossins et al.

(10) Patent No.: US 10,030,238 B2
(45) Date of Patent: Jul. 24, 2018

(54) RECOMBINANT CLOSTRIDIUM BOTULINUM NEUROTOXINS

(71) Applicant: Ipsen Bioinnovation Ltd., Abingdon, Oxfordshire (GB)

(72) Inventors: Aimee Cossins, Abingdon (GB); Matthew Beard, Abingdon (GB); Philip Marks, Wrexham (GB)

(73) Assignees: IPSEN BIOINNOVATION LIMITED, Abingdon, Oxfordshire (GB); IPSEN BIOPHARM LIMITED, Slough, Berkshire (GB)

( * ) Notice: Subject to any disclaimer, the term of this patent is extended or adjusted under 35 U.S.C. 154(b) by 0 days.

(21) Appl. No.: 14/427,234

(22) PCT Filed: Oct. 31, 2013

(86) PCT No.: PCT/GB2013/052845
§ 371 (c)(1),
(2) Date: Mar. 10, 2015

(87) PCT Pub. No.: WO2014/068317
PCT Pub. Date: May 8, 2014

(65) Prior Publication Data
US 2015/0247139 A1    Sep. 3, 2015

(30) Foreign Application Priority Data

Oct. 31, 2012 (GB) .................................. 1219602.8

(51) Int. Cl.
*C12N 9/52* (2006.01)
*A61K 38/00* (2006.01)

(52) U.S. Cl.
CPC ........ *C12N 9/52* (2013.01); *C12Y 304/24069* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,495,143 B2 | 12/2002 | Lee et al. | |
| 6,967,088 B1 * | 11/2005 | Williams | C07K 14/245 424/236.1 |
| 7,132,259 B1 | 11/2006 | Dolly et al. | |
| 7,514,088 B2 * | 4/2009 | Steward | A61K 38/4886 424/184.1 |
| 7,825,233 B2 * | 11/2010 | Steward | C07K 14/33 435/325 |
| 2004/0142455 A1 | 7/2004 | Williams | |
| 2005/0100973 A1 | 5/2005 | Steward et al. | |
| 2007/0166332 A1 * | 7/2007 | Steward | C07K 14/33 424/239.1 |
| 2008/0103098 A1 | 5/2008 | Specht | |
| 2008/0138893 A1 * | 6/2008 | Steward | C07K 14/33 435/325 |
| 2011/0111483 A1 | 5/2011 | Steward et al. | |
| 2012/0207743 A1 | 8/2012 | Jacky et al. | |

FOREIGN PATENT DOCUMENTS

| | | |
|---|---|---|
| WO | 0114570 A1 | 3/2001 |
| WO | 2006/011966 A1 | 2/2006 |
| WO | 2008/008805 A2 | 1/2008 |
| WO | 2009/014854 A1 | 1/2009 |
| WO | 2010/090677 A1 | 8/2010 |

OTHER PUBLICATIONS

Zalucki et al., 2011, Coupling between codon usage, translation and protein export in *Escherichia coli*, Biotechnology Journal, 6: 660-667.*
Brackley et al., 2010, Slow sites in an exclusion process with limited resources, Physical Review, 82: 051920 (13 pages).*
Dong et al., 2007, Towards a Model for Protein Production Rates, Journal of Statistical Physics, 128(1/2): 21-34.*
Chou et al., 2004, Clustered Bottlenecks in mRNA Translation and Protein Synthesis, Physical Review Letters, 93(19): 198101 (4 pages).*
Ponnala, 2010, Detecting slow-translating regions in *E. coli*, Int. J. Bioinformatics Researchand Applications, 6(5): 522-530.*
M.A. Gilmore, et al., "Fully active recombinant Bont/E purified from *E. coli* in high yield", Toxicon, Jun. 1, 2008, pp. 11-12, vol. 51,Elmsford, NY, US.
E. Angov, "Codon usage: Nature's roadmap to expression and folding of proteins", Biotechnology Journal, May 12, 2011, pp. 650-659, vol. 6, No. 6, Silver Spring, MD US.
S. Navon, et al., "The role of codon selection in regulation of translation efficiency deduced from synthetic libraries", Genome Biology, Biomed Central Ltd., Feb. 1, 2011, pp. R12, vol. 12, No. 2, London, GB.
C.A. Brackley, et al., "The Dynamics of Supply and Demand in mRNA Translation", PLoS Comp. Biol., Oct. 2011, pp. 1-16, vol. 7(10), Arberdeen, GB.
A. Fischer et al., "Molecular Architecture of Botulinum Neurotoxin E Revealed by Single Particle Electron Microscopy", Journal of Biological Chemistry, Feb. 15, 2008, pp. 3997-4003, vol. 283(7), The American Society for Biochemistry and Molecular Biology, Inc., USA.

(Continued)

*Primary Examiner* — Amber D Steele
(74) *Attorney, Agent, or Firm* — Davdi A. Kelly; Gene J. Yao; Barnes & Thornburg LLP

(57) ABSTRACT

The invention provides a nucleic acid sequence comprising a sequence of contiguous nucleotides, wherein said sequence of contiguous nucleotides has at least 90% sequence identity to the nucleic acid sequence of SEQ ID NO: 1, and wherein said sequence of contiguous nucleotides encodes a single-chain BoNT/E1 protein. The present invention also provides methods for producing soluble single-chain BoNT/E1 protein in an *E. coli* host cell, together with methods for producing soluble di-chain BoNT/E1 protein.

21 Claims, 13 Drawing Sheets

(56) References Cited

OTHER PUBLICATIONS

Figure 2A:
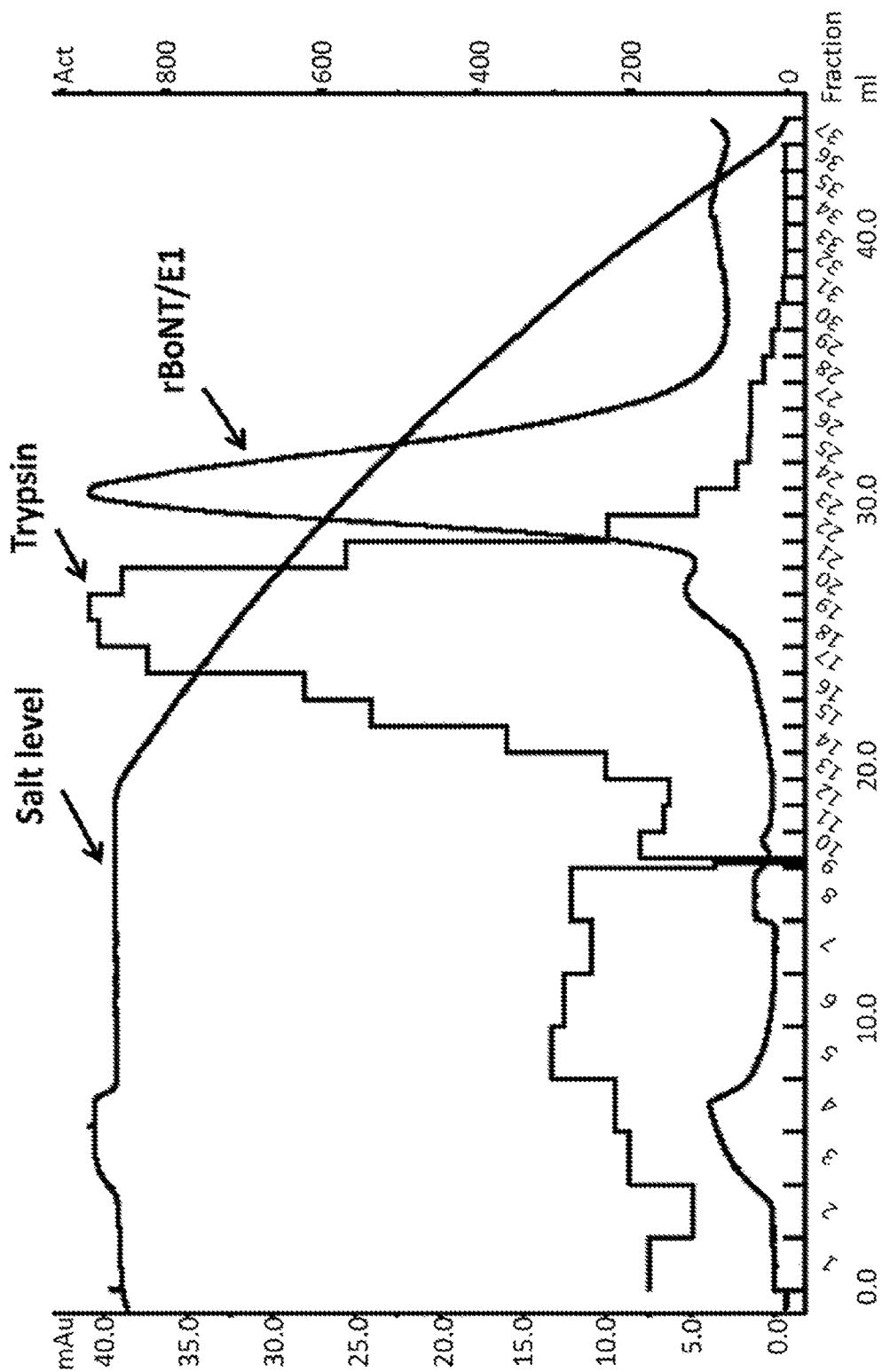

BXE_CLOBU, Primary Accession No. P30995, Prokaryotic Protein Annotation Program, Last Modified Jan. 7, 2015 URL: http://www.uniprot.org/uniprot/P30995.

Kukreja, Roshan V., et al., "Molecular Basis of Activation of Endopeptidase Activity of Botulinum Neurotoxin Type E", Biochemistry, dated 2010, 49, pp. 2510-2519, DOI: 10.1021/bi902096r.

* cited by examiner

```
SEQ ID NO: 1  ATGCCGAAAATCAACTCTTTCAACTACAACGACCCGGTTAACGACCGTACCATCCTGTAT 60
SEQ ID NO: 3  ATGCCAAAAATTAATAGTTTTAATTATAATGATCCTGTTAATGATAGAACAATTTTATAT 60
SEQ ID NO: 1  ATCAAACCGGGTGGTTGCCAGGAGTTCTACAAATCTTTCAACATCATGAAAAACATCTGG 120
SEQ ID NO: 3  ATTAAACCAGGCGGTTGTCAAGAATTTTATAAATCATTTAATATTATGAAAAATATTTGG 120
SEQ ID NO: 1  ATCATCCCGGAACGTAACGTTATCGGTACCACCCCGCAGGACTTCCACCCGCCGACCTCT 180
SEQ ID NO: 3  ATAATTCCAGAGAGAAATGTAATTGGTACAACCCCCCAAGATTTTCATCCGCCTACTTCA 180
SEQ ID NO: 1  CTGAAAAACGGTGACTCTTCTTACTACGACCCGAACTACCTCCAGTCTGACGAAGAAAAA 240
SEQ ID NO: 3  CTAAAAAATGGAGATAGTAGTTATTATGACCCTAATTATTTACAAAGTGATGAAGAAAAG 240
SEQ ID NO: 1  GACCGTTTCCTGAAAATCGTTACCAAAATCTTCAACCGTATCAACAACAACCTGTCTGGT 300
SEQ ID NO: 3  GATAGATTTTTAAAAATAGTCACAAAAATATTTAATAGAATAAACAATAATCTTTCAGGA 300
SEQ ID NO: 1  GGTATCCTGCTGGAAGAACTGTCTAAAGCTAACCCGTACCTGGGTAACGACAACACCCCG 360
SEQ ID NO: 3  GGGATTTTATTAGAAGAACTGTCAAAAGCTAATCCATATTTAGGGAATGATAATACTCCA 360
SEQ ID NO: 1  GACAACCAGTTCCACATCGGTGACGCTTCTGCTGTTGAAATCAAATTCTCTAACGGTTCT 420
SEQ ID NO: 3  GATAATCAATTCCATATTGGTGATGCATCAGCAGTTGAGATTAAATTCTCAAATGGTAGC 420
SEQ ID NO: 1  CAGGACATCCTGCTGCCGAACGTTATCATCATGGGTGCTGAACCGGACCTGTTCGAAACC 480
SEQ ID NO: 3  CAAGACATACTATTACCTAATGTTATTATAATGGGAGCAGAGCCTGATTTATTTGAAACT 480
SEQ ID NO: 1  AACTCTTCTAACATCTCTCTGCGTAACAACTACATGCCGTCTAACCACGGTTTCGGTTCT 540
SEQ ID NO: 3  AACAGTTCCAATATTTCTCTAAGAAATAATTATATGCCAAGCAATCACGGTTTTGGATCA 540
SEQ ID NO: 1  ATCGCTATCGTTACCTTCTCTCCGGAATACTCTTTCCGTTTCAACGACAACAGCATGAAC 600
SEQ ID NO: 3  ATAGCTATAGTAACATTCTCACCTGAATATTCTTTTAGATTTAATGATAATAGTATGAAT 600
SEQ ID NO: 1  GAGTTCATCCAGGACCCGGCTCTGACCCTGATGCACGAACTGATCCACTCTCTGCACGGT 660
SEQ ID NO: 3  GAATTTATTCAAGATCCTGCTCTTACATTAATGCATGAATTAATACATTCATTACATGGA 660
SEQ ID NO: 1  CTGTACGGTGCTAAAGGTATCACCACCAAATACACCATCACCCAGAAACAGAACCCGCTG 720
SEQ ID NO: 3  CTATATGGGGCTAAAGGGATTACTACAAAGTATACTATAACACAAAAACAAAATCCCCTA 720
SEQ ID NO: 1  ATCACCAACATCCGTGGTACCAACATCGAAGAGTTCCTGACCTTCGGTGGTACCGACCTG 780
SEQ ID NO: 3  ATAACAAATATAAGAGGTACAAATATTGAAGAATTCTTAACTTTTGGAGGTACTGATTTA 780
SEQ ID NO: 1  AACATCATCACCTCTGCTCAGTCTAACGACATCTACACCAACCTGCTGGCTGACTACAAA 840
SEQ ID NO: 3  AACATTATTACTAGTGCTCAGTCCAATGATATCTATACTAATCTTCTAGCTGATTATAAA 840
SEQ ID NO: 1  AAAATCGCTTCTAAACTGTCTAAAGTTCAGGTTTCTAACCCGCTGCTGAACCCGTACAAA 900
SEQ ID NO: 3  AAAATAGCGTCTAAACTTAGCAAAGTACAAGTATCTAATCCACTACTTAATCCTTATAAA 900
SEQ ID NO: 1  GACGTTTTCGAAGCTAAATACGGTCTGGACAAAGACGCTTCTGGTATCTACTCTGTTAAC 960
SEQ ID NO: 3  GATGTTTTTGAAGCAAAGTACGGATTAGATAAAGATGCTAGCGGAATTTATTCGGTAAAT 960
SEQ ID NO: 1  ATCAACAAATTCAACGACATCTTCAAAAAACTGTACTCTTTCACCGAGTTCGACCTGGCG 1020
SEQ ID NO: 3  ATAAACAAATTTAATGATATTTTTAAAAAATTATACAGCTTTACGGAATTTGATTTAGCA 1020
SEQ ID NO: 1  ACCAAATTCCAGGTTAAATGCCGTCAGACCTACATCGGTCAGTACAAATACTTCAAACTG 1080
SEQ ID NO: 3  ACTAAATTTCAAGTTAAATGTAGGCAAACTTATATTGGACAGTATAAATACTTCAAACTT 1080
```

Fig. 5B

```
SEQ ID NO: 1  TCTAACCTGCTGAACGACTCTATCTACAACATCTCTGAAGGTTACAACATCAACAACCTG 1140
              ||  | ||| || ||  |   ||| ||  ||||| || ||| || | | || || |  |
SEQ ID NO: 3  TCAAACTTGTTAAATGATTCTATTTATAATATATCAGAAGGCTATAATATAAATAATTTA 1140

SEQ ID NO: 1  AAAGTTAACTTCCGTGGTCAGAACGCTAACCTGAACCCGCGTATCATCACCCCGATCACC 1200
              |||| ||| ||  |  |||||||| |||| |||| | | ||||| | || ||| || ||
SEQ ID NO: 3  AAGGTAAATTTTAGAGGACAGAATGCAAATTTAAATCCTAGAATTATTACACCAATTACA 1200

SEQ ID NO: 1  GGTCGTGGTCTGGTTAAAAAAATCATCCGTTTCTGCAAGAATATTGTAAGCGTTAAAGGA 1260
              ||| | | |||||| ||||||||||| || |||||  ||||||| ||   |||||  | 
SEQ ID NO: 3  GGTAGAGGACTAGTAAAAAAAATCATTAGATTTTGTAAAAATATTGTTTCTGTAAAAGGC 1260

SEQ ID NO: 1  ATAAGAAAAGTATCTGCATCGAAATCAACAACGGTGAACTGTTCTTCGTTGCTTCTGAA 1320
              ||||| |||  ||| | ||||||||  || || |||| |||  |||| ||| || ||
SEQ ID NO: 3  ATAAGGAAATCAATATGTATCGAAATAAATAATGGTGAGTTATTTTTGTGGCTTCCGAG 1320

SEQ ID NO: 1  AACTCTTACAACGACGACAACATCAACACCCCGAAAGAAATCGACGACACCGTTACCTCT 1380
              ||   ||| |  | ||  || |||| ||  | ||||||| | |||| || ||| || ||
SEQ ID NO: 3  AATAGTTATAATGATGATAATATAAATACTCCTAAAGAAATTGACGATACAGTAACTTCA 1380

SEQ ID NO: 1  AACAACAACTACGAAAACGACCTGGACCAGGTTATCCTGAACTTCAACTCTGAATCTGCT 1440
              ||   |||||| |||| ||| | || ||| ||| |  ||| | | | ||| ||||| ||
SEQ ID NO: 3  AATAATAATTATGAAAATGATTTAGATCAGGTTATTTTAAATTTTAATAGTGAATCAGCA 1440

SEQ ID NO: 1  CCGGGTCTGTCTGACGAAAAACTGAACCTGACCATCCAGAACGACGCTTACATCCCGAAA 1500
              || | ||| | || ||||||| ||  |||  | ||| | || |||| ||||||||||||
SEQ ID NO: 3  CCTGGACTTTCAGATGAAAAATTAAATTTAACTATCCAAAATGATGCTTATATCCCAAAA 1500

SEQ ID NO: 1  TACGACTCTAACGGTACCTCTGACATCGAACAGCACGACGTTAACGAACTGAACGTTTTC 1560
              || || ||||| || ||    || || || ||  | || ||||| ||||| || |||||
SEQ ID NO: 3  TATGATTCTAATGGAACAAGTGATATAGAACAACATGATGTTAATGAACTTAATGTATTT 1560

SEQ ID NO: 1  TTCTACCTGGACGCTCAGAAAGTTCCGGAAGGTGAAAACAACGTTAACCTGACCTCTTCT 1620
              |||| | |||| || ||||||||  | ||||||||| ||  |||| ||  | || ||| 
SEQ ID NO: 3  TTCTATTTAGATGCACAGAAAGTGCCCGAAGGTGAAAAATAATGTCAATCTCACCTCTTCA 1620

SEQ ID NO: 1  ATCGACACCGCTCTGCTGGAACAGCCGAAAATCTACACCTTCTTCTCTTCTGAGTTCATC 1680
              || || || || || | |||| | || ||| | ||   |||||| ||| |||| || | 
SEQ ID NO: 3  ATTGATACAGCATTATTAGAACAACCTAAAATATATACATTTTTTTCATCAGAATTTATT 1680

SEQ ID NO: 1  AACAACGTTAACAAACCGGTTCAGGCTGCTCTGTTCGTTTCTTGGATTCAGCAGGTTCTG 1740
              || || ||||| ||| | || || || || ||| |  | | | ||| ||| || ||| |
SEQ ID NO: 3  AATAATGTCAATAAACCTGTGCAAGCAGCATTATTTGTAAGCTGGATACAACAAGTGTTA 1740

SEQ ID NO: 1  GTTGACTTCACCACCGAAGCTAACCAGAAATCTACCGTTGACAAAATCGCTGACATCTCT 1800
              ||  | |||||  ||||||||||| || |    | ||||| |||| | || || ||| |
SEQ ID NO: 3  GTAGATTTTACTACTGAAGCTAACCAAAAAAAGTACTGTTGATAAAATTGCAGATATTTCT 1800

SEQ ID NO: 1  ATCGTTGTTCCGTACATCGGTCTGGCTCTGAACATCGGTAACGAAGCTCAGAAAGGTAAC 1860
              || |  ||||| || |||| || || ||  |   | || |  || ||  ||||  |||
SEQ ID NO: 3  ATAGTTGTTCCATATATAGGTCTTGCTTTAAATATAGGAAATGAAGCACAAAAAGGAAAT 1860

SEQ ID NO: 1  TTCAAAGACGCTCTGGAACTGCTGGGTGCTGGTATCCTGCTGGAGTTCGAACCGGAACTG 1920
              |  ||||  |  |||||  | || || || || ||  |  |||| ||  ||| ||| ||
SEQ ID NO: 3  TTTAAAGATGCACTTGAATTATTAGGAGCAGGTATTTTATTAGAATTTGAACCCGAGCTT 1920

SEQ ID NO: 1  CTGATCCCGACCATCCTGGTTTTCACCATCAAATCTTTCCTGGGTTCTTCTGACAACAAA 1980
                || ||  ||  ||||| || | | || ||||||||  | || || || ||| |||||
SEQ ID NO: 3  TTAATTCCTACAATTTTAGTATTCACGATAAAATCTTTTTAGGTTCATCTGATAATAAA 1980

SEQ ID NO: 1  AACAAAGTTATCAAAGCTATCAACAACGCTCTGAAAGAACGTGACGAAAAATGGAAAGAA 2040
              ||  ||||||   ||||  ||| ||  | || ||||| ||| | ||||| |||||||||
SEQ ID NO: 3  AATAAAGTTATTAAAGCAATAAATAATGCATTGAAAGAAAGAGATGAAAAATGGAAAGAA 2040

SEQ ID NO: 1  GTTTACTCTTTCATCGTTTCTAACTGGATGACCAAAATCAACACCCAGTTCAACAAACGT 2100
              |  ||   |||| | || || ||||| ||||||| |||| ||  | |||||| |||  |
SEQ ID NO: 3  GTATATAGTTTTATAGTATCGAATTGGATGACTAAAATTAATACACAATTTAATAAAAGA 2100
```

Fig. 5C

```
SEQ ID NO: 1   AAAGAACAGATGTACCAGGCTCTCCAGAACCAGGTTAACGCTATCAAAACCATCATCGAA 2160
               |||||||| | ||||| |||| ||| ||||| ||| ||  ||||||  |||||| | |||
SEQ ID NO: 3   AAAGAACAAATGTATCAAGCTTTACAAAATCAAGTAAATGCAATTAAAACAATAATAGAA 2160
SEQ ID NO: 1   TCTAAATACAACTCTTACACCCTGGAAGAAAAAAACGAACTGACCAACAAATACGACATC 2220
               ||||| || || | |||| | | || || |||||| ||| ||  ||||| || |||| |
SEQ ID NO: 3   TCTAAGTATAATAGTTATACTTTAGAGGAAAAAAATGAGCTTACAAATAAATATGATATT 2220
SEQ ID NO: 1   AAACAGATCGAAAACGAACTGAACCAGAAAGTTTCTATCGCTATGAACAACATCGACCGT 2280
               || || ||  |||| ||||| || || |||  ||||||  ||| || ||||| | | ||
SEQ ID NO: 3   AAGCAAATAGAAAATGAACTTAATCAAAAGGTTTCTATAGCAATGAATAATATAGACAGG 2280
SEQ ID NO: 1   TTCCTGACCGAATCTTCTATCTCTTACCTGATGAAACTCATCAACGAAGTTAAAATCAAC 2340
               ||| | || ||| ||||||||  |||| || ||||   ||||||  ||| |||| ||||
SEQ ID NO: 3   TTCTTAACTGAAAGTTCTATATCCTATTTAATGAAATTAATAAATGAAGTAAAAATTAAT 2340
SEQ ID NO: 1   AAACTGCGTGAATACGACGAAAACGTTAAAACCTACCTGCTGAACTACATCATCCAGCAC 2400
               ||| | ||| || || |||||||| ||||| || |  ||||||| ||||| ||| | ||
SEQ ID NO: 3   AAATTAAGAGAATATGATGAGAATGTCAAAACGTATTTATTGAATTATATTATACAACAT 2400
SEQ ID NO: 1   GGTTCTATCCTGGGTGAATCTCAGCAGGAACTGAACTCTATGGTTACCGACACCCTGAAC 2460
               || ||||| ||||| || |||    ||||||  ||||||||| ||| |||||| |||  
SEQ ID NO: 3   GGATCAATCTTGGGAGAGAGTCAGCAAGAACTAAATTCTATGGTAACTGATACCCTAAAT 2460
SEQ ID NO: 1   AACTCTATCCCGTTCAAACTGTCTTCTTACACCGACGACAAAATCCTGATCTCTTACTTC 2520
               ||  |||| || ||||||| || ||||||||  |||||||||| |  | ||| ||| ||  
SEQ ID NO: 3   AATAGTATTCCTTTTAAGCTTTCTTCTTATACAGATGATAAAATTTTAATTTCATATTTT 2520
SEQ ID NO: 1   AACAAATTCTTTAAACGCATTAAGAGTTCATCGGTTCTGAATATGCGGTACAAAAATGAT 2580
               ||  ||||||||||| || ||||| |||| | |||||||| ||||| || ||||||||| 
SEQ ID NO: 3   AATAAATTCTTTAAGAGAATTAAAAGTAGTTCAGTTTTAAATATGAGATATAAAAATGAT 2580
SEQ ID NO: 1   AAATATGTCGATACTTCTGGATATGATAGCAATATCAACATTAACGGCGACGTGTATAAA 2640
               ||||| || ||||| ||  ||||||| || |||||  ||  | ||  |||||| ||| | 
SEQ ID NO: 3   AAATACGTAGATACTTCAGGATATGATTCAAATATAAATATTAATGGAGATGTATATAAA 2640
SEQ ID NO: 1   TATCCGACAAATAAAAACCAGTTTGGGATATATAACGACAAGCTGTCGGAGGTCAATATT 2700
               |||||| ||  || ||| |||  |||||||||| ||||| |||||| || || |||||| 
SEQ ID NO: 3   TATCCAACTAATAAAAATCAATTTGGAATATATAATGATAAACTTAGTGAAGTTAATATA 2700
SEQ ID NO: 1   TCTCAAAACGACTATATCATTTACGATAATAAATATAAAAACTTTAGCATTAGTTTTTGG 2760
               ||||||||  |||||| ||| | ||||||||||||||||||  |||||  |||| |||||
SEQ ID NO: 3   TCTCAAAATGATTACATTATATATGATAATAAATATAAAAATTTTAGTATTAGTTTTTGG 2760
SEQ ID NO: 1   GTTCGTATACCTAATTATGACAATAAAATTGTAAATGTGAATAACGAGTATACCATTATA 2820
               || | || || || ||||| |||||| |  || |||||||  || || || || |||||
SEQ ID NO: 3   GTAAGAATTCCTAACTATGATAATAAGATAGTAAATGTTAATAATGAATACACTATAATA 2820
SEQ ID NO: 1   AACTGTATGCGCGACAATAACAGTGGTTGGAAGGTATCGCTGAACCATAATGAGATTATC 2880
               || |||||  | |||| ||  ||  |||| |  ||||| ||||  ||||||||| ||| 
SEQ ID NO: 3   AATTGTATGAGAGATAATAATTCAGGATGGAAAGTATCTCTTAATCATAATGAAATAATT 2880
SEQ ID NO: 1   TGGACCCTGCAGGATAATGCAGGTATAAACCAGAAACTGGCTTTTAACTATGGAAACGCA 2940
               |||||  |||||||||||| ||| ||||  ||||| |||| ||||||||||| |||||| 
SEQ ID NO: 3   TGGACATTGCAAGATAATGCAGGAATTAATCAAAAATTAGCATTTAACTATGGTAACGCA 2940
SEQ ID NO: 1   AATGGGATCTCAGATTACATTAATAAATGGATTTTTGTTACCATTACGAACGATCGCTTA 3000
               |||||  | || ||||| ||  |||||| |||||||| ||| |||  |||| || |||
SEQ ID NO: 3   AATGGTATTTCTGATTATATAAATAAGTGGATTTTTGTAACTATAACTAATGATAGATTA 3000
SEQ ID NO: 1   GGCGACTCAAAACTTTATATTAATGGCAATCTGATAGATCAGAAATCAATCTTAAATTTG 3060
               ||  | || ||||||||||| |||| ||| || || ||||| ||| || |||| ||||| 
SEQ ID NO: 3   GGAGATTCTAAACTTTATATTAATGGAAATTTAATAGATCAAAAATCAATTTTAAATTTA 3060
SEQ ID NO: 1   GGCAATATTCATGTCTCTGATAACATCTTGTTCAAGATCGTTAATTGCAGTTACACTCGT 3120
               || ||||||||||| | ||| || ||| ||| | || || ||||| | ||||||| | |
SEQ ID NO: 3   GGTAATATTCATGTTAGTGACAATATATTATTTAAAATAGTTAATTGTAGTTATACAAGA 3120
```

Fig. 5D

```
SEQ ID NO: 1  TATATTGGCATTCGTTACTTTAATATCTTCGATAAAGAACTGGACGAGACGGAAATCCAG 3180
SEQ ID NO: 3  TATATTGGTATTAGATATTTTAATATTTTGATAAAGAATTAGATGAAACAGAAATTCAA  3180
SEQ ID NO: 1  ACTCTGTATTCAAACGAGCCCAATACTAATATATTGAAAGATTTTTGGGGTAACTATCTT 3240
SEQ ID NO: 3  ACTTTATATAGCAATGAACCTAATACAAATATTTTGAAGGATTTTTGGGGAAATTATTTG 3240
SEQ ID NO: 1  TTATATGATAAAGAATACTATCTCCTGAATGTATTGAAGCCAAACAATTTCATAGATAGA 3300
SEQ ID NO: 3  CTTTATGACAAAGAATACTATTTATTAAATGTGTTAAAACCAAATAACTTTATTGATAGG 3300
SEQ ID NO: 1  CGCAAGGATAGCACATTAAGTATCAACAATATCAGATCTACTATACTGTTAGCAAATCGC 3360
SEQ ID NO: 3  AGAAAAGATTCTACTTTAAGCATTAATAATATAAGAAGCACTATTCTTTTAGCTAATAGA 3360
SEQ ID NO: 1  CTCTACTCCGGTATTAAAGTGAAGATTCAGCGGGTTAATAACTCCAGTACCAATGATAAT 3420
SEQ ID NO: 3  TTATATAGTGGAATAAAAGTTAAAATACAAAGAGTTAATAATAGTAGTACTAACGATAAT 3420
SEQ ID NO: 1  CTGGTCCGTAAGAACGATCAGGTATACATCAATTTCGTCGCGAGCAAAACTCATCTCTTC 3480
SEQ ID NO: 3  CTTGTTAGAAAGAATGATCAGGTATATATTAATTTTGTAGCCAGCAAAACTCACTTATTT 3480
SEQ ID NO: 1  CCGCTTTACGCCGATACAGCTACGACAAACAAGGAAAAAACCATAAAAATTTCCAGCTCC 3540
SEQ ID NO: 3  CCATTATATGCTGATACAGCTACCACAAATAAAGAGAAAACAATAAAAATATCATCATCT 3540
SEQ ID NO: 1  GGAAACAGATTCAATCAAGTAGTTGTAATGAACTCTGTGGGTAATAATTGTACGATGAAC 3600
SEQ ID NO: 3  GGCAATAGATTTAATCAAGTAGTAGTTATGAATTCAGTAGGAAATAATTGTACAATGAAT 3600
SEQ ID NO: 1  TTTAAGAATAACAATGGGAACAATATTGGACTTTTGGGCTTCAAAGCCGACACAGTGGTG 3660
SEQ ID NO: 3  TTTAAAAATAATAATGGAAATAATATTGGGTTGTTAGGTTTCAAGGCAGATACTGTAGTT 3660
SEQ ID NO: 1  GCGTCCACCTGGTATTACACGCACATGCGGGACCATACGAATTCGAACGGTTGCTTCTGG 3720
SEQ ID NO: 3  GCTAGTACTTGGTATTATACACATATGAGAGATCATACAAACAGCAATGGATGTTTTTGG 3720
SEQ ID NO: 1  AACTTTATCTCGGAAGAACACGGGTGGCAAGAAAAATAA 3759
SEQ ID NO: 3  AACTTTATTTCTGAAGAACATGGATGGCAAGAAAAATAA 3759
```

Fig. 6A

```
SEQ ID NO: 1  ATGCCGAAAAATCAACTCTTTCAACTACAACGACCCGGTTAACGACCGTACCATCCTGTATATCAAACCGGGTGGTTGCCAGGAGTTCTACAAATCTTTCAACATCATGAA
SEQ ID NO: 2  M  P  K  I  N  S  F  N  Y  N  D  P  V  N  D  R  T  I  L  Y  I  K  P  G  G  C  Q  E  F  Y  K  S  F  N  I  M  K                                                    110
SEQ ID NO: 1  AAACATCTGGATCATCCCGGAACGTAACGTTATCGGTACCACCCCGCAGGACTTCCACCCGCCGACCTCTCTGAAAAACGGTGACTCTTCTTACTACGACCCGAACTACC
SEQ ID NO: 2  N  I  W  I  I  P  E  R  N  V  I  G  T  T  P  Q  D  F  H  P  P  T  S  L  K  N  G  D  S  S  Y  Y  D  P  N  Y                                                       220
SEQ ID NO: 1  TCCAGTCTGACGAAGAAAAAGACCGTTTCCTGAAAATCGTTACCAAAATCTTCAACCGTATCAACAACAACCTGTCTGGTGGTATCCTGCTGGAAGAACTGTCTAAAGCT
SEQ ID NO: 2  L  Q  S  D  E  E  K  D  R  F  L  K  I  V  T  K  I  F  N  R  I  N  N  N  L  S  G  G  I  L  L  E  E  L  S  K  A                                                    330
SEQ ID NO: 1  AACCCGTACCTGGGTAACGACAACACCCCGGACAACCAGTTCCACATCGGTGACGCTTCTGCTGTTGAAATCAAATTCTCTAACGGTTCTCAGGACATCCTGCTGCCGAA
SEQ ID NO: 2  N  P  Y  L  G  N  D  N  T  P  D  N  Q  F  H  I  G  D  A  S  A  V  E  I  K  F  S  N  G  S  Q  D  I  L  L  P  N                                                    440
SEQ ID NO: 1  CGTTATCATCATGGGTGCTGAACCGGACCTGTTCGAAACCAACTCTTCTAACATCTCTCTGCGTAACAACTACATGCCGTCTAACCACGGTTTCGGTTCTATCGCTATCG
SEQ ID NO: 2  V  I  I  M  G  A  E  P  D  L  F  E  T  N  S  S  N  I  S  L  R  N  N  Y  M  P  S  N  H  G  F  G  S  I  A  I                                                       550
SEQ ID NO: 1  TTACCTTCTCTCCGGAATACTCTTTCCGTTTCAACGACAACAGCATGAACGAGTTCATCCAGGACCCGGCTCTGACCCTGATGCACGAACTGATCCACTCTCTGCACGGT
SEQ ID NO: 2  V  T  F  S  P  E  Y  S  F  R  F  N  D  N  S  M  N  E  F  I  Q  D  P  A  L  T  L  M  H  E  L  I  H  S  L  H  G                                                    660
SEQ ID NO: 1  CTGTACGGTGCTAAAGGTATCACCACCAAATACACCATCACCCAGAAACAGAACCCGCTGATCACCAACATCCGTGGTACCAACATCGAAGAGTTCCTGACCTTCGGTGG
SEQ ID NO: 2  L  Y  G  A  K  G  I  T  T  K  Y  T  I  T  Q  K  Q  N  P  L  I  T  N  I  R  G  T  N  I  E  E  F  L  T  F  G  G                                                    770
SEQ ID NO: 1  TACCGACCTGAACATCATCACCTCTGCTCAGTCTAACGACATCTACACCAACCTGCTGGCTGACTACAAAAAAATCGCTTCTAAACTGTCTAAAGTTCAGGTTTCTAACC
SEQ ID NO: 2  T  D  L  N  I  I  T  S  A  Q  S  N  D  I  Y  T  N  L  L  A  D  Y  K  K  I  A  S  K  L  S  K  V  Q  V  S  N                                                       880
SEQ ID NO: 1  CGCTGCTGAACCCGTACAAAGACGTTTTCGAAGCTAAATACGGTCTGGACAAAGACGCTTCTGGTATCTACTCTGTTAACATCAACAAATTCAACGACATCTTCAAAAAA
SEQ ID NO: 2  P  L  L  N  P  Y  K  D  V  F  E  A  K  Y  G  L  D  K  D  A  S  G  I  Y  S  V  N  I  N  K  F  N  D  I  F  K  K                                                    990
SEQ ID NO: 1  CTGTACTCTTTCACCGAGTTCGACCTGGCGACCAAATTCCAGGTTAAATGCCGTCAGACCTACATCGGTCAGTACAAATACTTCAAACTGTCTAACCTGCTGAACGACTC
SEQ ID NO: 2  L  Y  S  F  T  E  F  D  L  A  T  K  F  Q  V  K  C  R  Q  T  Y  I  G  Q  Y  K  Y  F  K  L  S  N  L  L  N  D  S                                                    1100
SEQ ID NO: 1  TATCTACAACATCTCTGAAGGTTACAACATCAACAACCTGAAAGTTAACTTCCGTGGTCAGAACGCTAACCTGAACCCGCGTATCATCACCCCGATCACCGGTCGTGTC
SEQ ID NO: 2  I  Y  N  I  S  E  G  Y  N  I  N  N  L  K  V  N  F  R  G  Q  N  A  N  L  N  P  R  I  I  T  P  I  T  G  R  G                                                       1210
SEQ ID NO: 1  TGGTTAAAAAAAATCATCCGTTTCTGCAAGAATATTGTAAGCGTTAAAGGAATAAGAAAAAGTATCTGCATCGAAATCAACAACGGTGAACTGTTCTTCGTTGCTTCTGAA
SEQ ID NO: 2  L  V  K  K  I  I  R  F  C  K  N  I  V  S  V  K  G  I  R  K  S  I  C  I  E  I  N  N  G  E  L  F  F  V  A  S  E                                                    1320
SEQ ID NO: 1  AACTCTTACAACGACGACAACATCAACACCCCGAAAGAAATCGACGACACCGTTACCTCTAACAACAACTACGAAAACGACCTGGACCAGGTTATCCTGAACTTCAACTC
SEQ ID NO: 2  N  S  Y  N  D  D  N  I  N  T  P  K  E  I  D  D  T  V  T  S  N  N  N  Y  E  N  D  L  D  Q  V  I  L  N  F  N  S                                                    1430
SEQ ID NO: 1  TGAATCTGCTCCGGGTCTGTCTGACGAAAAACTGAACCTGACCATCCAGAACGACGCTTACATCCCGAAATACGACTCTAACGGTACCTCTGACATCGAACAGCACGACG
SEQ ID NO: 2  E  S  A  P  G  L  S  D  E  K  L  N  L  T  I  Q  N  D  A  Y  I  P  K  Y  D  S  N  G  T  S  D  I  E  Q  H  D                                                       1540
SEQ ID NO: 1  TTAACGAACTGAACGTTTTCTTCTACCTGGACGCTCAGAAAGTTCCGGAAGGTGAAAACAACGTTAACCTGACCTCTTCTATCGACACCGCTCTGCTGGAACAGCCGAAA
SEQ ID NO: 2  V  N  E  L  N  V  F  F  Y  L  D  A  Q  K  V  P  E  G  E  N  N  V  N  L  T  S  S  I  D  T  A  L  L  E  Q  P  K                                                    1650
SEQ ID NO: 1  ATCTACACCTTCTTCTCTTCTGAGTTCATCAACAACGTTAACAAACCGGTTCAGGCTGCTCTGTTCGTTTCTTGGATTCAGCAGGTTCTGGTTGACTTCACCACCGAAGC
SEQ ID NO: 2  I  Y  T  F  F  S  S  E  F  I  N  N  V  N  K  P  V  Q  A  A  L  F  V  S  W  I  Q  Q  V  L  V  D  F  T  T  E  A                                                    1760
SEQ ID NO: 1  TAACCAGAAAATCTACCGTTGACAAAATCGCTGACATCTCTATCGTTGTTCCGTACATCGGTCTGGCTCTGAACATCGGTAACGAAGCTCAGAAAGGTAACTTCAAAGACG
SEQ ID NO: 2  N  Q  K  S  T  V  D  K  I  A  D  I  S  I  V  V  P  Y  I  G  L  A  L  N  I  G  N  E  A  Q  K  G  N  F  K  D                                                       1870
SEQ ID NO: 1  CTCTGGAACTGCTGGGTGCTGGTATCCTGCTGGAGTTCGAACCGGAACTGCTGATCCCGACCATCCTGGTTTTCACCATCAAATCTTTCCTGGGTTCTTCTGACAACAAA
SEQ ID NO: 2  A  L  E  L  L  G  A  G  I  L  L  E  F  E  P  E  L  L  I  P  T  I  L  V  F  T  I  K  S  F  L  G  S  S  D  N  K                                                    1980
```

Fig. 6B

```
SEQ ID NO: 1  AACAAAGTTATCAAAGCTATCAACAACGCTCTGAAAGAACGTGACGAAAAATGGAAAGAAGTTTACTCTTTCATCGTTTCTAACTGGATGACCAAAATCAACACCCAGTT  2090
SEQ ID NO: 2   N K V I K A I N N A L K E R D E K W K E V Y S F I V S N W M T K I N T Q F

SEQ ID NO: 1  CAACAAACGTAAAGAACAGATGTACCAGGCTCTCCAGAACCAGGTTAACGCTATCAAAACCATCATCGAATCTAAATACAACTCTTACACCCTGGAAGAAAAAACGAAC  2200
SEQ ID NO: 2   N K R K E Q M Y Q A L Q N Q V N A I K T I I E S K Y N S Y T L E E K N E

SEQ ID NO: 1  TGACCAACAAATACGACATCAAACAGATCGAAAACGAACTGAACCAGAAAGTTTCTATCGCTATGAACAACATCGACCGTTTCCTGACCGAATCTTCTATCTCTTACCTG  2310
SEQ ID NO: 2   L T N K Y D I K Q I E N E L N Q K V S I A M N N I D R F L T E S S I S Y L

SEQ ID NO: 1  ATGAAACTCATCAACGAAGTTAAAATCAACAAACTGCGTGAATACGACGAAAACGTTAAAACCTACCTGCTGAACTACATCATCCAGCACGGTTCTATCCTGGGTGAATC  2420
SEQ ID NO: 2   M K L I N E V K I N K L R E Y D E N V K T Y L L N Y I I Q H G S I L G E S

SEQ ID NO: 1  TCAGCAGGAACTGAACTCTATGGTTACCGACACCCTGAACAACTCTATCCCGTTCAAACTGTCTTCTTACACCGACGACAAAATCCTGATCTCTTACTTCAACAAATTCT  2530
SEQ ID NO: 2   Q Q E L N S M V T D T L N N S I P F K L S S Y T D D K I L I S Y F N K F

SEQ ID NO: 1  TTAAACGCATTAAGAGTTCATCGGTTCTGAATATGCGGTACAAAAATGAT AAATATGTCGATACTTCTGGATATGATAGCAATATCAACATTAACGGCGACGTGTATAAA  2640
SEQ ID NO: 2   F K R I K S S S V L N M R Y K N D K Y V D T S G Y D S N I N I N G D V Y K

SEQ ID NO: 1  TATCCGACAAATAAAAACCAGTTTGGGATATATAACGACAAGCTGTCGGAGGTCAATATTTCTCAAAACGACTATATCATTTACGATAATAAATATAAAAACTTTAGCAT  2750
SEQ ID NO: 2   Y P T N K N Q F G I Y N D K L S E V N I S Q N D Y I I Y D N K Y K N F S I

SEQ ID NO: 1  TAGTTTTTGGGTTCGTATACCTAATTATGACAATAAAATTGTAAATGTGAATAACGAGTATACCATTATAAACTGTATGCGCGACAATAACAGTGGTTGGAAGGTATCGC  2860
SEQ ID NO: 2   S F W V R I P N Y D N K I V N V N N E Y T I I N C M R D N N S G W K V S

SEQ ID NO: 1  TGAACCATAATGAGATTATCTGGACCCTGCAGGATAATGCAGGTATAAACCAGAAACTGGCTTTTAACTATGGAAACGCAAATGGGATCTCAGATTACATTAATAAATGG  2970
SEQ ID NO: 2   L N H N E I I W T L Q D N A G I N Q K L A F N Y G N A N G I S D Y I N K W

SEQ ID NO: 1  ATTTTTGTTACCATTACGAACGATCGCTTAGGCGACTCAAAACTTTATATTAATGGCAATCTGATAGATCAGAAATCAATCTTAAATTTGGGCAATATTCATGTCTCTGA  3080
SEQ ID NO: 2   I F V T I T N D R L G D S K L Y I N G N L I D Q K S I L N L G N I H V S D

SEQ ID NO: 1  TAACATCTTGTTCAAGATCGTTAATTGCAGTTACACTCGTTATATTGGCATTCGTTACTTTAATATCTTCGATAAAGAACTGGACGAGACGGAAATCCAGACTCTGTATT  3190
SEQ ID NO: 2   N I L F K I V N C S Y T R Y I G I R Y F N I F D K E L D E T E I Q T L Y

SEQ ID NO: 1  CAAACGAGCCCAATACTAATATATTGAAAGATTTTTGGGGTAACTATCTTTTATATGATAAAGAATACTATCTCCTGAATGTATTGAAGCCAAACAATTTCATAGATAGA  3300
SEQ ID NO: 2   S N E P N T N I L K D F W G N Y L L Y D K E Y Y L L N V L K P N N F I D R

SEQ ID NO: 1  CGCAAGGATAGCACATTAAGTATCAACAATATCAGATCTACTATACTGTTAGCAAATCGCCTCTACTCCGGTATTAAAGTGAAGATTCAGCGGGTTAATAACTCCAGTAC  3410
SEQ ID NO: 2   R K D S T L S I N N I R S T I L L A N R L Y S G I K V K I Q R V N N S S T

SEQ ID NO: 1  CAATGATAATCTGGCCGTAAGAACGATCAGGTATACATCAATTTCGTCGCGAGCAAAACTCATCTCTTCCCGCTTTACGCCGATACAGCTACGACAAACAAGGAAAAAA  3520
SEQ ID NO: 2   N D N L V R K N D Q V Y I N F V A S K T H L F P L Y A D T A T T N K E K

SEQ ID NO: 1  CCATAAAAATTTCCAGCTCCGGAAACAGATTCAATCAAGTAGTTGTAATGAACTCTGTGGGTAATAATTGTACGATGAACTTTAAGAATAACAATGGGAACAATATTGGA  3630
SEQ ID NO: 2   T I K I S S S G N R F N Q V V V M N S V G N N C T M N F K N N N G N N I G

SEQ ID NO: 1  CTTTTGGGCTTCAAAGCCGACACAGTGGTGGCGTCCACCTGGTATTACACGCACATGCGGGACCATACGAATTCGAACGGTTGCTTCTGGAACTTTATCTCGGAAGAACA  3740
SEQ ID NO: 2   L L G F K A D T V V A S T W Y Y T H M R D H T N S N G C F W N F I S E E H

SEQ ID NO: 1  CGGGTGGCAAGAAAAATAA
SEQ ID NO: 2   G W Q E K
```

RECOMBINANT CLOSTRIDIUM BOTULINUM NEUROTOXINS

This application is a U.S. National Stage of International Application No. PCT/GB2013/052845, filed on 31 Oct. 2013, pending, which claims priority to GB 1219602.8 filed on 31 Oct. 2012. Each of the above-referenced applications is hereby incorporated by reference in its entirety.

The instant application contains a Sequence Listing which has been submitted electronically in ASCII format and is hereby incorporated by reference in its entirety. Said ASCII copy, created on Mar. 30, 2017, is named 58767_000930_SL.txt and is 22,941 bytes in size.

Pursuant to the provisions of 37 C.F.R. § 1.52(e)(5), the sequence listing text file named 103768_Seq_Lstng.txt, created on Mar. 9, 2015 and having a size of 21,198 bytes, and which is being submitted herewith, is incorporated by reference herein in its entirety.

The present invention relates to nucleic acid sequences encoding *Clostridium botulinum* (*C. botulinum*) neurotoxins of serotype E (BoNT/E), and to methods for producing recombinant BoNT/E. The present invention also relates to corresponding medical uses of a recombinant BoNT/E.

Botulinum neurotoxin is produced by *C. botulinum* in the form of a large protein complex, consisting of BoNT itself complexed to a number of accessory proteins. There are at present seven different classes of botulinum neurotoxin, namely: botulinum neurotoxin serotypes A, B, $C_1$, D, E, F and G, all of which share similar structures and modes of action. Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

BoNTs are the most potent toxins known, with median lethal dose (LD50) values for mice ranging from 0.5 to 5 ng/kg depending on the serotype. BoNTs are adsorbed in the gastrointestinal tract, and, after entering the general circulation, bind to the presynaptic membrane of cholinergic nerve terminals and prevent the release of their neurotransmitter acetylcholine. BoNT/B, BoNT/D, BoNT/F and BoNT/G cleave synaptobrevin/vesicle-associated membrane protein (VAMP); BoNT/C, BoNT/A and BoNT/E cleave the synaptosomal-associated protein of 25 kDa (SNAP-25); and BoNT/C cleaves syntaxin.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site, that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises a C-terminal targeting component ($H_C$ domain) and an N-terminal translocation component ($H_N$ domain). The cleavage site is located between the L-chain and the translocation components. Following binding of the $H_C$ domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically-cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of Clostridial neurotoxins are non-cytotoxic proteases that cleave SNARE proteins.

Botulinum neurotoxins are well known for their ability to cause a flaccid muscle paralysis. Said muscle-relaxant properties have led to botulinum neurotoxins (such as BoNT/A) being employed in a variety of medical and cosmetic procedures, including treatment of glabellar lines or hyperkinetic facial lines, headache, hemifacial spasm, hyperactivity of the bladder, hyperhidrosis, nasal labial lines, cervical dystonia, blepharospasm, and spasticity.

Traditionally, production of BoNT is carried out by culture of *C. botulinum* bacteria, followed by isolation and purification of the botulinum neurotoxin complex. However, production of BoNT in this way is inefficient and provides low protein yields. In addition, *C. botulinum* are spore-forming bacteria and therefore require specialist culture equipment and facilities, which are not required for the culture of bacteria such as *Escherichia coli* (*E. coli*). The increasing use of BoNTs has therefore led to a need for alternative and/or improved methods for producing and purifying BoNT.

US 20080103098 describes a method for producing recombinant BoNT proteins in a di-chain form comprising expression of a recombinant nucleic acid construct in an *E. coli* host cell. However, said method requires the insertion of a specific, non-native (i.e. non-clostridial) pentapeptide sequence into a loop domain of the neurotoxin. The inserted pentapeptide sequence forms an activation cleavage site that is cleaved by an endogenous *E. coli* protease upon cell lysis. The method of US 20080103098 therefore teaches that in order to achieve optimal BoNT expression, the BoNT sequence must be modified by the insertion of a non-native cleavage site.

U.S. Pat. No. 7,132,259 describes recombinant nucleic acid molecules encoding BoNT proteins. However, the nucleic acid molecules of U.S. Pat. No. 7,132,259 are modified to replace the native cleavage site with a non-native cleavage site. Thus, the method of U.S. Pat. No. 7,132,259 also teaches that insertion of a non-native cleavage site is required for optimal BoNT expression.

U.S. Pat. No. 6,495,143 describes recombinant nucleic acid molecules encoding fragments of the heavy chain ($H_C$) of a BoNT, for use in inducing immune responses (such as in vaccination). However, the nucleic acid molecules do not encode full length BoNT sequences. Expression in *E. coli* and purification of individual H and L chains of tetanus toxin and BoNT is achievable; these isolated chains are, by themselves, non-toxic. Following the separate production of these peptide chains and under strictly controlled conditions the H and L subunits can be combined by oxidative disulphide linkage to form active di-chains. Unfortunately, this strategy has several drawbacks. Firstly, it is not practical to express and isolate large amounts of the individual chains;

in particular, in the absence of the H-chain the isolated L-chain is quite insoluble in aqueous solution and is highly susceptible to proteolytic degradation. Secondly, the in vitro oxidation of the individually expressed and purified H and L chains to produce the active di-chain is very inefficient, and leads to low yields of active toxin and the production of many inactive incorrectly folded or oxidized forms. The purification of the correctly folded and oxidized H and L chain-containing toxin is difficult, as is its separation from these inactive forms and the unreacted separate H and L chains. Thus, the method of U.S. Pat. No. 6,495,143 is associated with considerable disadvantages.

There is therefore a need in the art for improved methods for producing recombinant BoNTs, in particular activated di-chain BoNTs recombinant BoNT/E.

The present invention solves one or more of the above-mentioned problems, by providing nucleic acid sequences and methods as specified in the claims.

In one aspect, the present invention provides a nucleic acid sequence comprising a sequence of contiguous nucleotides, wherein said sequence of contiguous nucleotides has at least 80% (for example, at least 80, 81, 82, 83, 84, 85, 86, 87, 88, 89, 90, 91, 92, 93, 94, 95, 96, 97, 98, 99, 99.5, 99.9, or 100%) sequence identity to the nucleic acid sequence of SEQ ID NO: 1, and wherein said sequence of contiguous nucleotides encodes a single-chain BoNT/E1 protein.

The BoNT/E serotype is divided into eight subtypes, BoNT/E1 to BoNT/E8, which share at least 90% amino acid sequence identity; BoNT/E proteins within a given subtype share a higher amino acid percentage sequence identity (for example, at least 95% or higher). As described above, the nucleic acid sequences of the invention encode a BoNT/E1 protein. An example of a BoNT/E1 protein is the protein encoded by UniParc amino acid sequence UPI000016EA7F. Another example of a BoNT/E1 protein is the protein encoded by the amino acid sequence of SEQ ID NO: 2.

The nucleic acid sequences of the present invention have been designed to advantageously provide high levels of expression in *E. coli* cells.

A number of factors influence expression levels of a given protein. One such factor is the rate at which the mRNA sequence encoding that protein is translated. This factor itself is affected by which particular codons the mRNA uses to specify each amino acid of the protein. Some codons are translated more quickly than others. The choice of codon for each amino acid can vary because mRNA codons are degenerate in nature. Several different codons can all specify the same amino acid; therefore several different mRNA sequences can encode the same protein. Different codons that specify the same amino acid are called synonymous codons. The precise mixture of synonymous codons in a particular mRNA affects the translation rate of the encoded protein.

There are a number of different reasons that account for why some codons are translated more quickly than others. Each codon specifies an amino acid by recruiting a tRNA molecule attached to that amino acid. The speed of translation is affected by the relative abundance of the various different tRNA molecules, by the affinity with which each particular tRNA molecule binds to the codon that recruits it and also by other factors such as how well the codon-tRNA molecule pair interacts with other elements of the translation machinery. Approximate codon translation rates can be estimated by determining the frequency at which different codons are found in highly-expressed genes. However, not all frequently occurring codons result in optimal expression.

Without wishing to be bound by any particular theory, the present inventors believe that optimal expression of BoNT/E1 nucleic acid sequences is achieved by reducing the frequency (i.e. the number of occurrences in a sequence) of certain codons, hereinafter deemed "slow codons" and set out below. In this regard, the present inventors believe that said slow codons are associated with reduced translation rates.

| Amino acid | Slow codon (RNA) | Slow codon (DNA equivalent) |
| --- | --- | --- |
| Phenylalanine | UUU | TTT |
| Tyrosine | UAU | TAT |
| Cysteine | UGU | TGT |
| Histidine | CAU | CAT |
| Glutamine | CAA | CAA |
| Proline | CCA and/or CCG | CCA and/or CCG |
| Serine | UCA and/or UCG | TCA and/or TCG |
| Arginine | CGG | CGG |
| Leucine | UUA and/or CUA | TTA and/or CTA |

The present inventors have employed a process of rational sequence design to produce the nucleic acid sequences of the invention. One way in which the nucleic acid sequences of the invention provide high expression levels of the encoded BoNT/E1 proteins is by having an optimised number of slow codons (for example, a reduction in the frequency at which slow codons appear in the sequence).

In one embodiment, the nucleic acid sequence has a maximum of 160 slow codons (for example, a maximum of 160, 150, 140, 130, 120, 110, 100, 90, 95, 94, 93, 92, 91, 90, 89, 88, or 87 slow codons).

Thus, in one embodiment, the nucleic acid sequence has between 0 and 160 slow codons (for example 0-160, 0-150, 0-140, 0-130, 0-120, 0-110, 0-100, 0-90, 0-95, 0-94, 0-93, 0-92, 0-91, 0-90, 0-89, 0-88, or 0-87 slow codons).

In one embodiment, the nucleic acid sequence has 60-160 slow codons (for example, 60-160, 60-150, 60-140, 70-150, 70-140, 70-130, 70-120, 70-110, 70-100, 70-90, 80-130, 80-120, 80-110, 80-100, or 80-90 slow codons).

In one embodiment, optionally in combination with any one or more of the above embodiments, there are fewer slow codons in the first 50% of the nucleic acid sequence than in the second 50% of the nucleic acid sequence. The first 50% of the nucleic acid sequence is defined with reference to nucleotide position number 1 as the starting point, and therefore comprises the site of translation initiation; the second 50% of the nucleic acid sequence comprises the site of translation termination. By way of example, referring to SEQ ID NO: 1 (which has a total length of 3759 nucleotides), the first half of said sequence may be represented by nucleotide positions 1-1881 (comprising 627 nucleotide triplets), and the second half of said sequence may be represented by positions 1882-3759 (comprising 626 nucleotide triplets); alternatively, the first half of said sequence may be represented by nucleotide positions 1-1878 (comprising 626 nucleotide triplets), and the second half of said sequence may be represented by positions 1879-3759 (comprising 627 nucleotide triplets).

In one embodiment, optionally in combination with any one or more of the above embodiments, the nucleic acid sequence (as described above) comprises a maximum of 30 (for example, 30, 25, 20, 15, or 10) phenylalanine slow codons (RNA=UUU; DNA=TTT). In one embodiment, optionally in combination with any one or more of the above embodiments, the nucleic acid sequence (as described above) comprises a maximum of 10 phenylalanine slow codons (RNA=UUU; DNA=TTT).

In one embodiment, optionally in combination with any one or more of the above embodiments (including the previously-described embodiments relating to phenylalanine slow codons), the nucleic acid sequence (as described above) comprises a maximum of 30 (for example, 30, 25, 20, 19, or 18) tyrosine slow codons (RNA=UAU; DNA=TAT). In one embodiment, optionally in combination with any one or more of the above embodiments (including the previously-described embodiments relating to phenylalanine slow codons), the nucleic acid sequence (as described above) comprises a maximum of 18 tyrosine slow codons (RNA=UAU; DNA=TAT).

In one embodiment, optionally in combination with any one or more of the above embodiments (including the previously-described embodiments relating to phenylalanine and/or tyrosine slow codons), the nucleic acid sequence (as described above) comprises a maximum of 19 (for example, 19, 18, 17, 16, 15, 12, 10, 9, 8, 7, 6, or 5) leucine slow codons (RNA=UUA and/or CUA; DNA=TTA and/or CTA). In one embodiment, optionally in combination with any one or more of the above embodiments (including the previously-described embodiments relating to phenylalanine and/or tyrosine slow codons), the nucleic acid sequence (as described above) comprises a maximum of 5 leucine slow codons (RNA=UUA and/or CUA; DNA=TTA and/or CTA).

In one embodiment, optionally in combination with any one or more of the above embodiments (including the previously-described embodiments relating to phenylalanine, tyrosine, and/or leucine slow codons), the nucleic acid sequence (as described above) comprises a maximum of 14 (for example, 14, 12, 10, 8, 6, 5, 4, or 3) glutamine slow codons (RNA=CAA; DNA=CAA). In one embodiment, optionally in combination with any one or more of the above embodiments (including the previously-described embodiments relating to phenylalanine, tyrosine, and/or leucine slow codons), the nucleic acid sequence (as described above) comprises a maximum of 3 glutamine slow codons (RNA=CAA; DNA=CAA).

In one embodiment, optionally in combination with any one or more of the above embodiments (including the previously-described embodiments relating to phenylalanine, tyrosine, leucine, and/or glutamine slow codons), the nucleic acid sequence (as described above) comprises a maximum of 20 (for example, 20, 19, 18, 17, or 16) serine slow codons (RNA=UCA and/or UCG; DNA=TCA and/or TCG). In one embodiment, optionally in combination with any one or more of the above embodiments (including the previously-described embodiments relating to phenylalanine, tyrosine, leucine, and/or glutamine slow codons), the nucleic acid sequence (as described above) comprises a maximum of 16 serine slow codons (RNA=UCA and/or UCG; DNA=TCA and/or TCG).

In one embodiment, optionally in combination with any one or more of the above embodiments (including the previously-described embodiments relating to phenylalanine, tyrosine, leucine, glutamine, and/or serine slow codons), the nucleic acid sequence (as described above) comprises a maximum of 23 (for example, 23, 22, 21, 20, or 19) proline slow codons (RNA=CCA and/or CCG; DNA=CCA and/or CCG). In one embodiment, optionally in combination with any one or more of the above embodiments (including the previously-described embodiments relating to phenylalanine, tyrosine, leucine, glutamine, and/or serine slow codons), the nucleic acid sequence (as described above) comprises a maximum of 19 proline slow codons (RNA=CCA and/or CCG; DNA=CCA and/or CCG).

In one embodiment, optionally in combination with any one or more of the above embodiments (including the previously-described embodiments relating to phenylalanine, tyrosine, leucine, glutamine, serine, and/or proline slow codons), the nucleic acid sequence (as described above) comprises a maximum of 3 (for example 3, or 2) cysteine slow codons (RNA=UGU; DNA=TGT. In one embodiment, optionally in combination with any one or more of the above embodiments (including the previously-described embodiments relating to phenylalanine, tyrosine, leucine, glutamine, serine, and/or proline slow codons), the nucleic acid sequence (as described above) comprises a maximum of 2 cysteine slow codons (RNA=UGU; DNA=TGT).

In one embodiment, optionally in combination with any one or more of the above embodiments (including the previously-described embodiments relating to phenylalanine, tyrosine, leucine, glutamine, serine, proline, and/or cysteine slow codons), the nucleic acid sequence (as described above) comprises a maximum of 5 (for example 5, or 4) histidine slow codons (RNA=CAU; DNA=CAT). In one embodiment, optionally in combination with any one or more of the above embodiments (including the previously-described embodiments relating to phenylalanine, tyrosine, leucine, glutamine, serine, proline, and/or cysteine slow codons), the nucleic acid sequence (as described above) comprises a maximum of 4 histidine slow codons (RNA=CAU; DNA=CAT).

In one embodiment, optionally in combination with any one or more of the above embodiments (including the previously-described embodiments relating to phenylalanine, tyrosine, leucine, glutamine, serine, proline, cysteine, and/or histidine slow codons), the nucleic acid sequence (as described above) comprises from 5 to 10 (for example, 5, 6, 7, 8, 9, or 10) arginine slow codons (RNA=CGG; DNA=CGG). In one embodiment, optionally in combination with any one or more of the above embodiments (including the previously-described embodiments relating to phenylalanine, tyrosine, leucine, glutamine, serine, proline, cysteine, and/or histidine slow codons), the nucleic acid sequence (as described above) comprises 10 arginine slow codons (RNA=CGG; DNA=CGG).

In one embodiment, optionally in combination with any one or more of the above embodiments, the nucleic acid sequence (as described above) comprises a maximum of 30 (for example, 30, 25, 20, 15, or 10; preferably 10) phenylalanine slow codons (RNA=UUU; DNA=TTT), and a maximum of 30 (for example, 30, 25, 20, 19, or 18; preferably 18) tyrosine slow codons (RNA=UAU; DNA=TAT).

In one embodiment, optionally in combination with any one or more of the above embodiments, the nucleic acid sequence (as described above) comprises a maximum of 30 (for example, 30, 25, 20, 15, or 10; preferably 10) phenylalanine slow codons (RNA=UUU; DNA=TTT), a maximum of 30 (for example, 30, 25, 20, 19, or 18; preferably 18) tyrosine slow codons (RNA=UAU; DNA=TAT), and a maximum of 19 (for example, 19, 18, 17, 16, 15, 12, 10, 9, 8, 7, 6, or 5; preferably 5) leucine slow codons (RNA=UUA and/or CUA; DNA=TTA and/or CTA).

In one embodiment, optionally in combination with any one or more of the above embodiments, the nucleic acid sequence (as described above) comprises a maximum of 30 (for example, 30, 25, 20, 15, or 10; preferably 10) phenylalanine slow codons (RNA=UUU; DNA=TTT), a maximum of 30 (for example, 30, 25, 20, 19, or 18; preferably 18)

tyrosine slow codons (RNA=UAU; DNA=TAT), a maximum of 19 (for example, 19, 18, 17, 16, 15, 12, 10, 9, 8, 7, 6, or 5; preferably 5) leucine slow codons (RNA=UUA and/or CUA; DNA=TTA and/or CTA), and a maximum of 14 (for example, 14, 12, 10, 8, 6, 5, 4, or 3; preferably 3) glutamine slow codons (RNA=CAA; DNA=CAA).

In one embodiment, optionally in combination with any one or more of the above embodiments, the nucleic acid sequence (as described above) comprises:
a maximum of 10 phenylalanine slow codons;
a maximum of 18 tyrosine slow codons;
a maximum of 2 cysteine slow codons;
a maximum of 4 histidine slow codons;
a maximum of 3 glutamine slow codons;
a maximum of 19 proline slow codons;
a maximum of 16 serine slow codons; and
a maximum of 5 leucine slow codons.

In one embodiment, optionally in combination with any one or more of the above embodiments, the nucleic acid sequence (as described above) comprises:
a maximum of 10 phenylalanine slow codons;
a maximum of 18 tyrosine slow codons;
a maximum of 2 cysteine slow codons;
a maximum of 4 histidine slow codons;
a maximum of 3 glutamine slow codons;
a maximum of 19 proline slow codons;
a maximum of 16 serine slow codons;
a maximum of 5 leucine slow codons; and
a maximum of 10 arginine slow codons.

In one embodiment, wherein the nucleic acid sequence is a nucleic acid sequence as described above, said single-chain BoNT/E1 protein comprises a sequence of contiguous amino acids, and wherein said sequence of contiguous amino acids has at least 95% (for example, at least 95, 96, 97, 98, 99, 99.1, 99.2, 99.3, 99.4, 99.5, 99.6, 99.7, 99.8, 99.9, or 100%) sequence identity to the amino acid sequence of SEQ ID NO: 2.

In one embodiment, wherein the nucleic acid sequence is a nucleic acid sequence as described above, said single chain BoNT/E1 protein comprises a native activation site that is provided by an amino acid sequence selected from: KGIRK (SEQ ID NO: 4), VKGIRKS (SEQ ID NO: 5), SVKGIRKSI (SEQ ID NO: 6), VSVKGIRKSI (SEQ ID NO: 7), IVSVK-GIRKSI (SEQ ID NO: 8), NIVSVKGIRKSI (SEQ ID NO: 9), KNIVSVKGIRKSI (SEQ ID NO: 10), CKNIVSVK-GIRKSIC (SEQ ID NO: 11).

In one embodiment, the nucleic acid sequence is a nucleic acid sequence as described above, with the proviso that the single-chain BoNT/E1 as described above or the sequence of contiguous amino acids as described above includes one or more (for example, one or more, two or more, three or more, four or more, five or more, six or more, seven or more, or eight) of the following amino acids (wherein the amino acid position numbering starts with the N-terminal amino acid residue and ends with the C-terminal amino acid residue of the BoNT/E1 protein):
glycine at position 177; serine at position 198; alanine at position 340; leucine at position 773; leucine at position 963; glutamine at position 964; alanine at position 967; asparagine at position 1195.

In one embodiment, said one or more amino acids comprise (or consist of) glycine at position 177; serine at position 198; alanine at position 340; leucine at position 773; leucine at position 963; glutamine at position 964; alanine at position 967; and asparagine at position 1195.

In one embodiment, said one or more amino acids comprise (or consist of) glycine at position 177; alanine at position 340; leucine at position 773; leucine at position 963; glutamine at position 964; alanine at position 967; and asparagine at position 1195.

In one embodiment, said one or more amino acids comprise (or consist of) glycine at position 177, and one or more (for example, one or more, two or more, three or more, four or more, five or more, six or more, or seven) of: serine at position 198; alanine at position 340; leucine at position 773; leucine at position 963; glutamine at position 964; alanine at position 967; asparagine at position 1195.

In one embodiment, said one or more amino acids comprise (or consist of) serine at position 198, and one or more (for example, one or more, two or more, three or more, four or more, five or more, six or more, or seven) of: glycine at position 177; alanine at position 340; leucine at position 773; leucine at position 963; glutamine at position 964; alanine at position 967; and asparagine at position 1195.

In one embodiment, said one or more amino acids comprise (or consist of) alanine at position 340, and one or more (for example, one or more, two or more, three or more, four or more, five or more, six or more, or seven) of: glycine at position 177; serine at position 198; leucine at position 773; leucine at position 963; glutamine at position 964; alanine at position 967; asparagine at position 1195.

In one embodiment, said one or more amino acids comprise (or consist of) leucine at position 773, and one or more (for example, one or more, two or more, three or more, four or more, five or more, six or more, or seven) of: glycine at position 177; serine at position 198; alanine at position 340; leucine at position 963; glutamine at position 964; alanine at position 967; asparagine at position 1195.

In one embodiment, said one or more amino acids comprise (or consist of) leucine at position 963, and one or more (for example, one or more, two or more, three or more, four or more, five or more, six or more, or seven) of: glycine at position 177; serine at position 198; alanine at position 340; leucine at position 773; glutamine at position 964; alanine at position 967; asparagine at position 1195.

In one embodiment, said one or more amino acids comprise (or consist of) glutamine at position 964, and one or more (for example, one or more, two or more, three or more, four or more, five or more, six or more, or seven) of: glycine at position 177; serine at position 198; alanine at position 340; leucine at position 773; leucine at position 963; alanine at position 967; asparagine at position 1195.

In one embodiment, said one or more amino acids comprise (or consist of) alanine at position 967, and one or more (for example, one or more, two or more, three or more, four or more, five or more, six or more, or seven) of: glycine at position 177; serine at position 198; alanine at position 340; leucine at position 773; leucine at position 963; glutamine at position 964; asparagine at position 1195.

In one embodiment, said one or more amino acids comprise (or consist of) asparagine at position 1195, and one or more (for example, one or more, two or more, three or more, four or more, five or more, six or more, or seven) of: glycine at position 177; serine at position 198; alanine at position 340; leucine at position 773; leucine at position 963; glutamine at position 964; alanine at position 967.

In one embodiment, the presence of said one or more amino acids, as described above, provides a BoNT/E1 protein having improved solubility as compared to a BoNT/E1 protein lacking said amino acids. Said improved solubility increases the yield of the protein in a heterologous (*E. coli*) expression system.

In one embodiment, wherein the nucleic acid sequence is a nucleic acid sequence as described above, the sequence of contiguous nucleotides has at least 770 (for example, at least 770, 775, 780, 785, 790, 795, 800, 810, 820, 830, 840, 850, 860, 870, or 880) synonymous codons when compared to the nucleic acid sequence of wild-type BoNT/E1 (SEQ ID NO: 3). Thus, in one embodiment, the nucleic acid sequence comprises at least 770 codons that differ from, but encode the same amino acid as, the corresponding codon in the nucleic acid sequence of wild-type BoNT/E1 (SEQ ID NO: 3).

In one embodiment, the nucleic acid sequence (as described above) has a G-C content of at least 41% (for example, at least 41 or 42%). In one embodiment, the nucleic acid sequence (as described above) has a G-C content of 42%. The concept of nucleic acid G-C content (also known as GC content or G+C content) relates to the proportion of nucleotides of a given nucleic acid sequence that are either G (guanine) or C (cytosine). Thus, in one embodiment, the G-C content of a nucleic acid sequence of the invention is altered (for example by substitution of synonymous codons) to more closely match the G-C content of nucleic acids preferentially expressed in E. coli host cells, thus improving expression of the sequence and providing increased protein yields.

In one aspect, the invention provides an expression vector encoding a nucleic acid sequence as described above. In one embodiment, the expression vector is a pET-26b(+) vector.

In one aspect, the invention provides a host cell comprising a nucleic acid sequence as described above, or an expression vector as described above. In one embodiment, the host cell is an E. coli cell. In one embodiment, the E. coli host cell is an E. coli BLR (DE3) cell.

In one aspect, the invention provides a method for producing soluble single-chain BoNT/E1 protein in an E. coli host cell, said method comprising: expressing a nucleic acid sequence (as described above) in an E. coli expression system.

Methods and techniques used to express heterologous proteins in E. coli (Escherichia coli) expression systems are well known in the art.

In one embodiment, said soluble single-chain BoNT/E1 protein is expressed in the cytoplasm of said E. coli host cell.

In one embodiment, said soluble single-chain BoNT/E1 protein is expressed at a level of at least 3 mg/L (for example, at least 3, 4, 5, 6, 7, 8, 9, 10, 15, 20, 25, 30, 25, 40, 45, or 50 mg/L).

In one embodiment, the method for producing soluble single-chain BoNT/E1 protein, as described above, comprises lysis of the E. coli host cell to provide an E. coli host cell homogenate containing said soluble single-chain BoNT/E1 protein. Methods and techniques used to lyse host cells, such as E. coli host cells, are known in the art. Examples include sonication and the use of a French press.

In one aspect, the invention provides a method for producing soluble di-chain BoNT/E1 protein, said method comprising: providing a soluble single-chain BoNT/E1 protein comprising a sequence of contiguous amino acids, and wherein said sequence of contiguous amino acids has at least 95% (for example, at least 95, 96, 97, 98, 99, 99.1, 99.2, 99.3, 99.4, 99.5, 99.6, 99.7, 99.8, 99.9, or 100%) sequence identity to the amino acid sequence of SEQ ID NO: 2, and contacting said BoNT/E1 protein with trypsin in solution.

When the single-chain BoNT/E1 protein of the invention is contacted with trypsin, the proteolytic action of trypsin cleaves the single-chain protein at a site between the L-chain protease component and the translocation component to produce a di-chain protein, where the two chains are linked by a disulphide bridge (in more detail, the two chains formed following cleavage of single-chain BoNT/E1 at the activation site are a first chain of amino acid residues 1-419 and a second chain of amino acid residues 423-1252, with residues 420, 421 and 422 removed by the cleavage event). Thus, trypsin can be used to activate the single-chain polypeptide by converting it to the active di-chain form. Thus, advantageously, the use of trypsin means that it is not necessary to engineer an exogenous (non-native) cleavage site into a BoNT/E1 of the invention.

In one embodiment, reference to trypsin embraces trypsin-like enzymes that cleave at the same protease cleavage site as trypsin.

Trypsin cleaves protein sequences in which particular amino acids lie at certain positions on either side of the cleaved peptide bond. Such sequences can be represented by the nomenclature P4-P3-P2-P1-cleaved bond-P'1-P'2-P'3-P'4; in which P1 to P4 designate amino acids positioned 1 to 4 positions to the N-terminal side of the cleaved peptide bond respectively and P' 1 to P'4 designate 1, to 4 positions C-terminal of the cleaved peptide bond respectively.

Most importantly Trypsin cleaves protein sequences where either Arg or Lys amino acids occupy the P1 position. When Lys is in the P1 position there are three major types of sequence that are not sensitive to trypsin:
(1) Pro in the P'1 position usually reduces susceptibility to cleavage by trypsin (but not when Trp is in position P2).
(2) Either Cys or Asp in the P2 position together with Asp in the P'1 position reduces susceptibility to cleavage by trypsin.
(3) Cys in the P2 position together with either His or Try in the P' 1 position reduces susceptibility to cleavage by trypsin When Arg is in the P1 position there are also three major types of sequence that are not sensitive to trypsin:
(1) Pro in the P'1 position usually reduces susceptibility to cleavage by trypsin (but not when either Met, or possibly Glu, is in position P2).
(2) Cys in the P2 position together with Lys in the P' 1 position reduces susceptibility to cleavage by trypsin.
(3) Arg in the P2 position together with either His or Arg in the P'1 position reduces susceptibility to cleavage by trypsin.

In one embodiment, the invention provides a method (as described above) for producing soluble di-chain BoNT/E1 protein, with the proviso that said sequence of contiguous amino acids includes one or more (for example, one or more, two or more, three or more, four or more, five or more, six or more, or seven) of the following amino acids (wherein the amino acid position numbering starts with the N-terminal amino acid residue and ends with the C-terminal amino acid residue of the BoNT/E1 protein): glycine at position 177; serine at position 198; alanine at position 340; leucine at position 773; leucine at position 963; glutamine at position 964; alanine at position 967; asparagine at position 1195.

In one embodiment, the presence of said one or more amino acids, as described above (and with reference to the multiple permutations of said one or more amino acids as described above), provides a BoNT/E1 protein having improved solubility as compared to a BoNT/E1 protein lacking said amino acids. Said improved solubility can increase the yield of the protein in a heterologous expression system.

In one embodiment, wherein the invention provides a method (as described above) for producing soluble di-chain BoNT/E1 protein, the soluble single-chain BoNT/E1 protein is provided by a method as described above for producing soluble single-chain BoNT/E1 protein in an *E. coli* host cell.

In one embodiment, wherein the invention provides a method (as described above) for producing soluble di-chain BoNT/E1 protein, the method comprises separating the soluble BoNT/E1 protein from the trypsin by contacting the solution containing soluble BoNT/E1 protein and trypsin with a hydrophobic surface, wherein the soluble BoNT/E1 protein preferentially binds to the hydrophobic surface.

The present inventors have found that high yields of activated di-chain BoNT/E1 protein can be obtained by using a process of hydrophobic purification to separate the activated di-chain polypeptide from trypsin. Surprisingly, this process provides superior purification to standard purification using ion exchange chromatography, which the present inventors have found to be ineffective for separating the activated di-chain polypeptide from trypsin. In addition, the process advantageously provides an activated di-chain BoNT/E1 protein that is free from the activating protease, as part of a general purification process.

The production of active recombinant BoNT/E1 requires a proteolytic step that cleaves the molecule into the active di-chain form. This cleavage can be achieved by an in vitro activation step using the protease, trypsin. After the activation step, it is important to remove the protease from the final product, which also prevents any further non-specific cleavage of BoNT/E1.

The isoelectric points (pI) of trypsin and BoNT/E1 are 9.32 and 6.2 respectively, which indicates that separation of the two proteins should be achieved by Ion Exchange (IEX) chromatography, exploiting the charge difference between the two molecules. A protein's net charge is affected by the pH of its surrounding environment and will become more positively or negatively charged depending on whether it gains or loses protons. The pI is the pH value at which a molecule carries no electrical charge and will therefore not interact with a charged IEX medium. This means that if a protein is at a pH above its pI then it will carry a net negative charge and will bind to a positively charged medium such as an anion exchanger. Similarly, if the buffer pH is below the pI then the protein will carry a net positive charge and will not bind to an anion exchanger.

Based on this principle at pH 8, it would be expected that BoNT/E (which has a pI of 6.2) would bind to an anion exchange column, whilst trypsin with a pI of 9.32 would not, allowing the two proteins to be separated. IEX is a simple and inexpensive chromatography method, as it does not require the protein loaded onto the column to be in a high salt buffer, which can lead to protein losses by precipitation.

The present inventors have tested a variety of anion exchange columns, using both strong and weak functional groups attached to cross-linked agarose beads, at pH 8. In each case a large proportion of trypsin was found not to bind to the column as predicted and was present in the flow-through. However when the columns were eluted with a linear gradient of increasing ionic strength, trypsin was eluted from the column indicating that a proportion of the trypsin was able to bind to the columns. When compared to the elution of BoNT/E1 it was found that, unexpectedly, trypsin eluted at a similar ionic strength (Table 1; FIG. 1) indicating that trypsin was not separated as predicted and would be present in the final purified BoNT/E1 product with the additional possibility of further BoNT/E1 degradation.

TABLE 1

Elution fractions from anion exchange columns on which the separation of trypsin from BoNT/E1 was assessed. Peaks are stated in number of column volumes (CV) F/T: Flow-through from the column, FF: Fast flow resin.

| Column | Trypsin | | BoNT/E1 | |
| --- | --- | --- | --- | --- |
| | Major Peak | Minor Peak | Major Peak | Minor Peak |
| ANX | F/T | 8.8, 11.3, 12.3 | 10.7 | 17.3 |
| QHP | F/T | 9.0, 10.6 | — | — |
| DEAE | F/T | 10.5 | 9.8 | 13.2 |
| Q FF | F/T | 9.2, 10.9 | 16.1 | 10.7 |

The present inventors have solved the above problem. In more detail, the inventors have surprisingly identified that optimal trypsin-BoNT/E1 separation is achieved by use of a hydrophobic separation surface (for example, by hydrophobic interaction chromatography (HIC), which separates proteins according to differences in their surface hydrophobicity by utilising a reversible interaction between these proteins and the hydrophobic surface of a HIC medium).

In one embodiment, the hydrophobic surface is an inert matrix to which a ligand consisting of aryl or alkyl groups is attached.

The term "aryl" refers to aromatic groups, for example phenyl, naphthyl, thienyl, and indolyl.

The term "alkyl" refers to aliphatic groups including straight-chain, branched-chain, cyclic groups, and combinations thereof. An alkyl group may have 1 to 12 carbon atoms. Examples of alkyl groups include, but are not limited to groups such as methyl, ethyl, propyl (e.g. n-propyl, isopropyl), butyl (e.g. n-butyl, isobutyl, sec-butyl, t-butyl), pentyl, hexyl, heptyl, and octyl.

In one embodiment, the hydrophobic surface is selected from the group consisting of: butyl, phenyl or octyl ligands.

In one embodiment, the hydrophobic surface comprises butyl ligands. In one embodiment, the hydrophobic surface comprises phenyl ligands. In one embodiment, the hydrophobic surface comprises octyl ligands.

The present inventors have discovered that particularly preferable results for separating trypsin from BoNT/E are obtained with HIC using chromatography resins containing alkyl or aryl groups, for example butyl, phenyl, and octyl ligands, coupled to an inert matrix, such as cross-linked agarose or polystyrene beads (Table 2; FIG. 2).

TABLE 2

Elution fractions from commercial hydrophobic interaction columns on which the separation of trypsin from BoNT/E was assessed. Peaks are stated in number of column volumes (CV) F/T: Flow-through from the column, FF: Fast flow resin, HP: High performance resin, (LS): Low substitution of hydrophobic groups, (HS): High substitution of hydrophobic groups.

| Column | Trypsin | | BoNT/E | |
| --- | --- | --- | --- | --- |
| | Major Peak | Minor Peak | Major Peak | Minor Peak |
| Phenyl (HS) FF | 23.3 | — | 32.2 | — |
| Phenyl (LS) FF | F/T | — | 21.4 | — |
| Phenyl HP | F/T | 16.1 | 24.4 | — |
| Butyl FF | F/T | 16.8 | 23.7 | — |
| Butyl HP | 18 | Wash | 27.6 | — |
| Octyl FF | F/T | — | 27.1 | — |

In one embodiment, the process of hydrophobic purification to separate the activated di-chain BoNT/E1 protein from trypsin reduces the concentration of trypsin at least 100-fold, at least 150-fold, at least 200-fold, at least 250-fold, at least 300-fold, at least 350-fold, at least 400-fold, at least 450-fold, or at least 500-fold. In a preferred embodiment, the process of hydrophobic purification to separate the activated di-chain BoNT/E1 protein from trypsin reduces the concentration of trypsin at least 350-fold.

In another aspect, the invention provides an active di-chain BoNT/E1 protein, wherein the first chain comprises a sequence of contiguous amino acids, and wherein said sequence of contiguous amino acids has at least 95% (for example, at least 95, 96, 97, 98, 99, 99.1, 99.2, 99.3, 99.4, 99.5, 99.6, 99.7, 99.8, 99.9, or 100%) sequence identity to the amino acid sequence of positions 1-419 of SEQ ID NO: 2; wherein the second chain comprises a sequence of contiguous amino acids, and wherein said sequence of contiguous amino acids has at least 95% (for example, at least 95, 96, 97, 98, 99, 99.1, 99.2, 99.3, 99.4, 99.5, 99.6, 99.7, 99.8, 99.9, or 100%) sequence identity to the amino acid sequence of positions 423-1252 of SEQ ID NO: 2; wherein the first and second chains are joined together by a disulphide bond between cysteine 412 on the first chain and cysteine 426 on the second chain; with the proviso that said sequence of contiguous amino acids includes one or more (for example, two or more, three or more, four or more, five or more, six or more, seven or more, or eight) of the following amino acids (wherein the amino acid position numbering starts with the N-terminal amino acid residue and ends with the C-terminal amino acid residue of the BoNT/E1 protein): glycine at position 177; serine at position 198; alanine at position 340; leucine at position 773; leucine at position 963; glutamine at position 964; alanine at position 967; asparagine at position 1195.

In a related aspect, the invention provides an active di-chain BoNT/E1 protein obtainable by a method (as described above) for producing soluble di-chain BoNT/E1 protein.

In one aspect, the invention provides a composition comprising an active di-chain BoNT/E1 protein (as described above), wherein said composition is substantially free from trypsin.

Thus, the composition is, advantageously, substantially free from trypsin protease (used to activate the single-chain polypeptide by converting it to the active di-chain form), thus preventing unwanted non-specific cleavage of BoNT/E1 protein.

In one embodiment, wherein the composition (as described above) is substantially free from trypsin, the composition contains less than 100 picograms (pg) trypsin per 100 nanograms (ng) of BoNT/E1 protein; for example, less than 50, 20, 10, 9, 8, 7, 6 or 5 pg trypsin per 100 ng of BoNT/E1 protein. In one embodiment, the composition (as described above) contains less than 10 pg trypsin per 100 ng of BoNT/E1 protein, or less than 7 pg trypsin per 100 ng of BoNT/E1 protein, or less than 5 pg trypsin per 100 ng of BoNT/E1 protein. In a preferred embodiment, the composition (as described above) contains less than 10 pg trypsin per 100 ng of BoNT/E1 protein, or less than 7 pg trypsin per 100 ng of BoNT/E1 protein.

Thus, in one embodiment, the phrase "substantially free from trypsin" means less than 100 pg trypsin per 100 ng of BoNT/E1 protein; for example, less than 50, 20, 10, 9, 8, 7, 6 or 5 pg trypsin per 100 ng of BoNT/E1 protein, preferably less than 10 pg trypsin per 100 ng of BoNT/E1 protein, or less than 7 pg trypsin per 100 ng of BoNT/E1 protein.

Methods for determining the concentration of trypsin in a composition are known in the art. By way of example, the concentration of trypsin in a composition of the invention may be determined using a sandwich ELISA (Enzyme-Linked Immunosorbent Assay).

In a further aspect, the present invention provides a solid or liquid pharmaceutical composition comprising:
(a) an active di-chain BoNT/E1 protein as described above, and
(b) a stabilising agent.

In one embodiment, the composition (as described above) is substantially free from trypsin. In one embodiment, the composition contains less than 100 pg trypsin per 100 ng of BoNT/E1 protein, for example, less than 50, 20, 10, 9, 8, 7, 6 or 5 pg trypsin per 100 ng of BoNT/E1 protein. In one embodiment, the composition contains less than 10 pg trypsin per 100 ng of BoNT/E1 protein, or less than 7 pg trypsin per 100 ng of BoNT/E1 protein.

Stabilising agents which can be used in compositions according to the invention include protein stabilisers, such as albumin, in particular human serum albumin (HSA), and non-protein stabilisers.

Non-protein stabilising agents which can be used in the composition according to the invention include surfactants, in particular non-ionic surfactants. Examples of non-ionic surfactants include polysorbates, such as polysorbate 20 or polysorbate 80, and block copolymers such as poloxamers (i.e. copolymers of polyethylene and propylene glycol).

In a particular embodiment, the composition does not comprise a protein as a stabilising agent.

According to a particular embodiment of the invention, the pharmaceutical composition is a liquid pharmaceutical composition comprising:
  (a) an active di-chain BoNT/E1 protein, as described above;
  (b) a non-protein stabilising agent that is a surfactant; and
  (c) water;
  wherein said liquid pharmaceutical composition does not comprise a protein stabilising agent; and
  wherein said liquid pharmaceutical composition is substantially free from trypsin (e.g. said liquid pharmaceutical composition contains less than 100 pg trypsin per 100 ng of BoNT/E1 protein, or less than 10 pg trypsin per 100 ng of BoNT/E1 protein, or less than 7 pg trypsin per 100 ng of BoNT/E1 protein, or less than 5 pg trypsin per 100 ng of BoNT/E1 protein; preferably wherein said liquid pharmaceutical composition contains less than 10 pg trypsin per 100 ng of BoNT/E1 protein, or less than 7 pg trypsin per 100 ng of BoNT/E1 protein).

In one embodiment, the active di-chain BoNT/E1 protein is present in the composition (as described above) at a concentration of 1-100 ng/ml. In one embodiment, the active di-chain BoNT/E1 protein is present in the composition (as described above) at a concentration of 5-50 ng/ml, e.g. about 5, 10, 15, 20, 25, 30, 35, 40, 45 or 50 ng/ml. In a preferred embodiment, the active di-chain BoNT/E1 protein is present at a concentration of about 20 ng/ml.

In one embodiment, the surfactant (as described above) is a polysorbate, such as a polysorbate having a mean polymerisation degree ranging from 20 to 100 monomer units, and may for example be polysorbate 80. In a preferred embodiment, the polysorbate is vegetable-derived. The concentration of the surfactant is preferably lower than 1% v/v, for example from about 0.005% to 0.02% v/v in the case of polysorbate 80.

The pharmaceutical composition according to the invention can also comprise a crystalline agent.

By crystalline agent is meant an agent which, inter alia, maintains a mechanically strong cake structure to a lyophilised botulinum neurotoxin complex (type A, B, C, D, E, F or G) or a high purity botulinum neurotoxin (type A, B, C, D, E, F or G). When included in solid formulations, crystalline agents also have a bulking effect. Crystalline agents notably include sodium chloride. The concentration of crystalline agent can be for example from 0.1 to 0.5 M, preferably from 0.1 to 0.4 M, notably about 0.15 to 0.3 M The pharmaceutical composition according to the invention can also comprise a buffer to maintain pH a level comprised between 5.5 and 7.5, or between 6.0 and 7.0. The buffer can be any buffer able to maintain the adequate pH. For example, the buffer for compositions according to the invention can be chosen from the group consisting of succinate, disodium phosphate/citric acid, and an amino acid such as histidine. The concentration of the buffer can be for example from 1 to 50 mM, preferably from 5 to 20 mM, preferably about 10 mM.

The pharmaceutical composition according to the invention can also comprise a disaccharide.

The disaccharide used in compositions according to the invention can be chosen from the group consisting of sucrose, trehalose, mannitol and lactose. In a specific embodiment, the disaccharide is sucrose. The concentration of the disaccharide can be for example from 5 to 50 mM, preferably from 5 to 25 mM, more preferably from 10 to 20 mM, and most preferably about 11.7 mM.

In a particular embodiment, the pharmaceutical composition is a liquid pharmaceutical composition comprising:
(a) an active di-chain BoNT/E1 protein, as described above;
(b) a non-protein stabilising agent that is a surfactant;
(c) sodium chloride,
(c) a buffer to maintain pH between 5.5 and 7.5
(e) a disaccharide, and
(f) sterile water.

wherein said liquid pharmaceutical composition does not comprise a protein stabilising agent; and
wherein said liquid pharmaceutical composition is substantially free from trypsin (e.g. said liquid pharmaceutical composition contains less than 100 pg trypsin per 100 ng of BoNT/E1 protein, or less than 10 pg trypsin per 100 ng of BoNT/E1 protein, or less than 7 pg trypsin per 100 ng of BoNT/E1 protein, or less than 5 pg trypsin per 100 ng of BoNT/E1 protein; preferably wherein said liquid pharmaceutical composition contains less than 10 pg trypsin per 100 ng of BoNT/E1 protein, or less than 7 pg trypsin per 100 ng of BoNT/E1 protein).

According to a specific embodiment, the pharmaceutical composition according to the invention in liquid form is sealed in a vial or in a ready-to-use device, such as a syringe, with no liquid/gaseous interface, and is stable for at least three months or at least six months at 23 to 27° C. and for at least twelve months at 2-8° C.

In one aspect, the invention provides an active di-chain BoNT/E1 protein as described above, or an active di-chain BoNT/E1 protein obtainable by proteolytic cleavage of the single-chain BoNT/E1 protein as described above, or a composition as described above, or a liquid pharmaceutical composition as described above, for use in therapy.

The present inventors have identified that the active di-chain BoNT/E1 proteins of the invention, and the compositions and liquid pharmaceutical compositions thereof, can be used in therapy. Suitable therapies may include cosmetic treatments and methods of medical treatment.

KEY TO SEQ ID NOS

SEQ ID NO: 1 Optimised BoNT/E1 nucleic acid sequence
SEQ ID NO: 2 BoNT/E1 amino acid sequence
SEQ ID NO: 3 Wildtype BoNT/E1 nucleic acid sequence

```
Optimised BoNT/E1 nucleic acid sequence
                                        SEQ ID NO: 1
ATGCCGAAAATCAACTCTTTCAACTACAACGACCCGGTTAACGACCGTACCATCCTGTAT

ATCAAACCGGGTGGTTGCCAGGAGTTCTACAAATCTTTCAACATCATGAAAAACATCTGG

ATCATCCCGGAACGTAACGTTATCGGTACCACCCCGCAGGACTTCCACCCGCCGACCTCT

CTGAAAAACGGTGACTCTTCTTACTACGACCCGAACTACCTCCAGTCTGACGAAGAAAAA

GACCGTTTCCTGAAAATCGTTACCAAAATCTTCAACCGTATCAACAACAACCTGTCTGGT

GGTATCCTGCTGGAAGAACTGTCTAAAGCTAACCCGTACCTGGGTAACGACAACACCCCG

GACAACCAGTTCCACATCGGTGACGCTTCTGCTGTTGAAATCAAATTCTCTAACGGTTCT

CAGGACATCCTGCTGCCGAACGTTATCATCATGGGTGCTGAACCGGACCTGTTCGAAACC

AACTCTTCTAACATCTCTCTGCGTAACAACTACATGCCGTCTAACCACGGTTTCGGTTCT

ATCGCTATCGTTACCTTCTCTCCGGAATACTCTTTCCGTTTCAACGACAACAGCATGAAC

GAGTTCATCCAGGACCCGGCTCTGACCCTGATGCACGAACTGATCCACTCTCTGCACGGT

CTGTACGGTGCTAAAGGTATCACCACCAAATACACCATCACCCAGAAACAGAACCCGCTG

ATCACCAACATCCGTGGTACCAACATCGAAGAGTTCCTGACCTTCGGTGGTACCGACCTG

AACATCATCACCTCTGCTCAGTCTAACGACATCTACACCAACCTGCTGGCTGACTACAAA

AAAATCGCTTCTAAACTGTCTAAAGTTCAGGTTTCTAACCCGCTGCTGAACCCGTACAAA

GACGTTTTCGAAGCTAAATACGGTCTGGACAAAGACGCTTCTGGTATCTACTCTGTTAAC

ATCAACAAATTCAACGACATCTTCAAAAAACTGTACTCTTTCACCGAGTTCGACCTGGCG

ACCAAATTCCAGGTTAAATGCCGTCAGACCTACATCGGTCAGTACAAATACTTCAAACTG
```

-continued

```
TCTAACCTGCTGAACGACTCTATCTACAACATCTCTGAAGGTTACAACATCAACAACCTG

AAAGTTAACTTCCGTGGTCAGAACGCTAACCTGAACCCGCGTATCATCACCCCGATCACC

GGTCGTGGTCTGGTTAAAAAAATCATCCGTTTCTGCAAGAATATTGTAAGCGTTAAAGGA

ATAAGAAAAGTATCTGCATCGAAATCAACAACGGTGAACTGTTCTTCGTTGCTTCTGAA

AACTCTTACAACGACGACAACATCAACACCCCGAAAGAAATCGACGACACCGTTACCTCT

AACAACAACTACGAAAACGACCTGGACCAGGTTATCCTGAACTTCAACTCTGAATCTGCT

CCGGGTCTGTCTGACGAAAAACTGAACCTGACCATCCAGAACGACGCTTACATCCCGAAA

TACGACTCTAACGGTACCTCTGACATCGAACAGCACGACGTTAACGAACTGAACGTTTTC

TTCTACCTGGACGCTCAGAAAGTTCCGGAAGGTGAAAACAACGTTAACCTGACCTCTTCT

ATCGACACCGCTCTGCTGGAACAGCCGAAAATCTACACCTTCTTCTCTTCTGAGTTCATC

AACAACGTTAACAAACCGGTTCAGGCTGCTCTGTTCGTTTCTTGGATTCAGCAGGTTCTG

GTTGACTTCACCACCGAAGCTAACCAGAAATCTACCGTTGACAAAATCGCTGACATCTCT

ATCGTTGTTCCGTACATCGGTCTGGCTCTGAACATCGGTAACGAAGCTCAGAAAGGTAAC

TTCAAAGACGCTCTGGAACTGCTGGGTGCTGGTATCCTGCTGGAGTTCGAACCGGAACTG

CTGATCCCGACCATCCTGGTTTTCACCATCAAATCTTTCCTGGGTTCTTCTGACAACAAA

AACAAAGTTATCAAAGCTATCAACAACGCTCTGAAAGAACGTGACGAAAAATGGAAAGAA

GTTTACTCTTTCATCGTTTCTAACTGGATGACCAAAATCAACACCCAGTTCAACAAACGT

AAAGAACAGATGTACCAGGCTCTCCAGAACCAGGTTAACGCTATCAAAACCATCATCGAA

TCTAAATACAACTCTTACACCCTGGAAGAAAAAAACGAACTGACCAACAAATACGACATC

AAACAGATCGAAAACGAACTGAACCAGAAAGTTTCTATCGCTATGAACAACATCGACCGT

TTCCTGACCGAATCTTCTATCTCTTACCTGATGAAACTCATCAACGAAGTTAAAATCAAC

AAACTGCGTGAATACGACGAAAACGTTAAAACCTACCTGCTGAACTACATCATCCAGCAC

GGTTCTATCCTGGGTGAATCTCAGCAGGAACTGAACTCTATGGTTACCGACACCCTGAAC

AACTCTATCCCGTTCAAACTGTCTTCTTACACCGACGACAAAATCCTGATCTCTTACTTC

AACAAATTCTTTAAACGCATTAAGAGTTCATCGGTTCTGAATATGCGGTACAAAAATGAT

AAATATGTCGATACTTCTGGATATGATAGCAATATCAACATTAACGGCGACGTGTATAAA

TATCCGACAAATAAAAACCAGTTTGGGATATATAACGACAAGCTGTCGGAGGTCAATATT

TCTCAAAACGACTATATCATTTACGATAATAAATATAAAAACTTTAGCATTAGTTTTTGG

GTTCGTATACCTAATTATGACAATAAAATTGTAAATGTGAATAACGAGTATACCATTATA

AACTGTATGCGCGACAATAACAGTGGTTGGAAGGTATCGCTGAACCATAATGAGATTATC

TGGACCCTGCAGGATAATGCAGGTATAAACCAGAAACTGGCTTTTAACTATGGAAACGCA

AATGGGATCTCAGATTACATTAATAAATGGATTTTTGTTACCATTACGAACGATCGCTTA

GGCGACTCAAAACTTTATATTAATGGCAATCTGATAGATCAGAAATCAATCTTAAATTTG

GGCAATATTCATGTCTCTGATAACATCTTGTTCAAGATCGTTAATTGCAGTTACACTCGT

TATATTGGCATTCGTTACTTTAATATCTTCGATAAAGAACTGGACGAGACGGAAATCCAG

ACTCTGTATTCAAACGAGCCCAATACTAATATATTGAAAGATTTTTGGGGTAACTATCTT

TTATATGATAAAGAATACTATCTCCTGAATGTATTGAAGCCAAACAATTTCATAGATAGA

CGCAAGGATAGCACATTAAGTATCAACAATATCAGATCTACTATACTGTTAGCAAATCGC

CTCTACTCCGGTATTAAAGTGAAGATTCAGCGGGTTAATAACTCCAGTACCAATGATAAT

CTGGTCCGTAAGAACGATCAGGTATACATCAATTTCGTCGCGAGCAAAACTCATCTCTTC
```

-continued

```
CCGCTTTACGCCGATACAGCTACGACAAACAAGGAAAAAACCATAAAAATTTCCAGCTCC

GGAAACAGATTCAATCAAGTAGTTGTAATGAACTCTGTGGGTAATAATTGTACGATGAAC

TTTAAGAATAACAATGGGAACAATATTGGACTTTTGGGCTTCAAAGCCGACACAGTGGTG

GCGTCCACCTGGTATTACACGCACATGCGGGACCATACGAATTCGAACGGTTGCTTCTGG

AACTTTATCTCGGAAGAACACGGGTGGCAAGAAAAATAA
```

BoNT/E1 amino acid sequence

SEQ ID NO: 2

```
MPKINSFNYNDPVNDRTILYIKPGGCQEFYKSFNIMKNIWIIPERNVIGTTPQDFHPPTS

LKNGDSSYYDPNYLQSDEEKDRFLKIVTKIFNRINNNLSGGILLEELSKANPYLGNDNTP

DNQFHIGDASAVEIKFSNGSQDILLPNVIIMGAEPDLFETNSSNISLRNNYMPSNHGFGS

IAIVTFSPEYSFRFNDNSMNEFIQDPALTLMHELIHSLHGLYGAKGITTKYTITQKQNPL

ITNIRGTNIEEFLTFGGTDLNIITSAQSNDIYTNLLADYKKIASKLSKVQVSNPLLNPYK

DVFEAKYGLDKDASGIYSVNINKFNDIFKKLYSFTEFDLATKFQVKCRQTYIGQYKYFKL

SNLLNDSIYNISEGYNINNLKVNFRGQNANLNPRIITPITGRGLVKKIIRFCKNIVSVKG

IRKSICIEINNGELFFVASENSYNDDNINTPKEIDDTVTSNNNYENDLDQVILNFNSESA

PGLSDEKLNLTIQNDAYIPKYDSNGTSDIEQHDVNELNVFFYLDAQKVPEGENNVNLTSS

IDTALLEQPKIYTFFSSEFINNVNKPVQAALFVSWIQQVLVDFTTEANQKSTVDKIADIS

IVVPYIGLALNIGNEAQKGNFKDALELLGAGILLEFEPELLIPTILVFTIKSFLGSSDNK

NKVIKAINNALKERDEKWKEVYSFIVSNWMTKINTQFNKRKEQMYQALQNQVNAIKTIIE

SKYNSYTLEEKNELTNKYDIKQIENELNQKVSIAMNNIDRFLTESSISYLMKLINEVKIN

KLREYDENVKTYLLNYIIQHGSILGESQQELNSMVTDTLNNSIPFKLSSYTDDKILISYF

NKFFKRIKSSSVLNMRYKNDKYVDTSGYDSNININGDVYKYPTNKNQFGIYNDKLSEVNI

SQNDYIIYDNKYKNFSISFWVRIPNYDNKIVNVNNEYTIINCMRDNNSGWKVSLNHNEII

WTLQDNAGINQKLAFNYGNANGISDYINKWIFVTITNDRLGDSKLYINGNLIDQKSILNL

GNIHVSDNILFKIVNCSYTRYIGIRYFNIFDKELDETEIQTLYSNEPNTNILKDFWGNYL

LYDKEYYLLNVLKPNNFIDRRKDSTLSINNIRSTILLANRLYSGIKVKIQRVNNSSTNDN

LVRKNDQVYINFVASKTHLFPLYADTATTNKEKTIKISSSGNRFNQVVVMNSVGNNCTMN

FKNNNGNNIGLLGFKADTVVASTWYYTHMRDHTNSNGCFWNFISEEHGWQEK
```

Wildtype BoNT/E1 nucleic acid sequence

SEQ ID NO: 3

```
ATGCCAAAAATTAATAGTTTTAATTATAATGATCCTGTTAATGATAGAACAATTTTATAT

ATTAAACCAGGCGGTTGTCAAGAATTTTATAAATCATTTAATATTATGAAAAATATTTGG

ATAATTCCAGAGAGAAATGTAATTGGTACAACCCCCCAAGATTTTCATCCGCCTACTTCA

TTAAAAAATGGAGATAGTAGTTATTATGACCCTAATTATTTACAAAGTGATGAAGAAAAG

GATAGATTTTTAAAAATAGTCACAAAAATATTTAATAGAATAAATAATAATCTTTCAGGA

GGGATTTTATTAGAAGAACTGTCAAAAGCTAATCCATATTTAGGGAATGATAATACTCCA

GATAATCAATTCCATATTGGTGATGCATCAGCAGTTGAGATTAAATTCTCAAATGGTAGC

CAAGACATACTATTACCTAATGTTATTATAATGGGAGCAGAGCCTGATTTATTTGAAACT

AACAGTTCCAATATTTCTCTAAGAAATAATTATATGCCAAGCAATCACGGTTTTGGATCA

ATAGCTATAGTAACATTCTCACCTGAATATTCTTTTAGATTTAATGATAATAGTATGAAT

GAATTTATTCAAGATCCTGCTCTTACATTAATGCATGAATTAATACATTCATTACATGGA

CTATATGGGGCTAAAGGGATTACTACAAAGTATACTATAACACAAAAACAAAATCCCCTA

ATAACAAATATAAGAGGTACAAATATTGAAGAATTCTTAACTTTTGGAGGTACTGATTTA
```

```
AACATTATTACTAGTGCTCAGTCCAATGATATCTATACTAATCTTCTAGCTGATTATAAA

AAAATAGCGTCTAAACTTAGCAAAGTACAAGTATCTAATCCACTACTTAATCCTTATAAA

GATGTTTTTGAAGCAAAGTATGGATTAGATAAAGATGCTAGCGGAATTTATTCGGTAAAT

ATAAACAAATTTAATGATATTTTTAAAAAATTATACAGCTTTACGGAATTTGATTTAGCA

ACTAAATTTCAAGTTAAATGTAGGCAAACTTATATTGGACAGTATAAATACTTCAAACTT

TCAAACTTGTTAAATGATTCTATTTATAATATATCAGAAGGCTATAATATAAATAATTTA

AAGGTAAATTTTAGAGGACAGAATGCAAATTTAAATCCTAGAATTATTACACCAATTACA

GGTAGAGGACTAGTAAAAAAAATCATTAGATTTTGTAAAAATATTGTTTCTGTAAAAGGC

ATAAGGAAATCAATATGTATCGAAATAAATAATGGTGAGTTATTTTTTGTGGCTTCCGAG

AATAGTTATAATGATGATAATATAAATACTCCTAAAGAAATTGACGATACAGTAACTTCA

AATAATAATTATGAAAATGATTTAGATCAGGTTATTTTAAATTTTAATAGTGAATCAGCA

CCTGGACTTTCAGATGAAAAATTAAATTTAACTATCCAAAATGATGCTTATATACCAAAA

TATGATTCTAATGGAACAAGTGATATAGAACAACATGATGTTAATGAACTTAATGTATTT

TTCTATTTAGATGCACAGAAAGTGCCCGAAGGTGAAAATAATGTCAATCTCACCTCTTCA

ATTGATACAGCATTATTAGAACAACCTAAAATATATACATTTTTTTCATCAGAATTTATT

AATAATGTCAATAAACCTGTGCAAGCAGCATTATTTGTAAGCTGGATACAACAAGTGTTA

GTAGATTTTACTACTGAAGCTAACCAAAAAAGTACTGTTGATAAAATTGCAGATATTTCT

ATAGTTGTTCCATATATAGGTCTTGCTTTAAATATAGGAAATGAAGCACAAAAAGGAAAT

TTTAAAGATGCACTTGAATTATTAGGAGCAGGTATTTTATTAGAATTTGAACCCGAGCTT

TTAATTCCTACAATTTTAGTATTCACGATAAAATCTTTTTTAGGTTCATCTGATAATAAA

AATAAAGTTATTAAAGCAATAAATAATGCATTGAAAGAAAGAGATGAAAAATGGAAAGAA

GTATATAGTTTTATAGTATCGAATTGGATGACTAAAATTAATACACAATTTAATAAAGA

AAAGAACAAATGTATCAAGCTTTACAAAATCAAGTAAATGCAATTAAAACAATAATAGAA

TCTAAGTATAATAGTTATACTTTAGAGGAAAAAAATGAGCTTACAAATAAATATGATATT

AAGCAAATAGAAAATGAACTTAATCAAAAGGTTTCTATAGCAATGAATAATATAGACAGG

TTCTTAACTGAAAGTTCTATATCCTATTTAATGAAATTAATAAATGAAGTAAAAATTAAT

AAATTAAGAGAATATGATGAGAATGTCAAAACGTATTTATTGAATTATATTATACAACAT

GGATCAATCTTGGGAGAGAGTCAGCAAGAACTAAATTCTATGGTAACTGATACCCTAAAT

AATAGTATTCCTTTTAAGCTTTCTTCTTATACAGATGATAAAATTTTAATTTCATATTTT

AATAAATTCTTTAAGAGAATTAAAAGTAGTTCAGTTTTAAATATGAGATATAAAAATGAT

AAATACGTAGATACTTCAGGATATGATTCAAATATAAATATTAATGGAGATGTATATAAA

TATCCAACTAATAAAAATCAATTTGGAATATATAATGATAAACTTAGTGAAGTTAATATA

TCTCAAAATGATTACATTATATATGATAATAAATATAAAAATTTTAGTATTAGTTTTTGG

GTAAGAATTCCTAACTATGATAATAAGATAGTAAATGTTAATAATGAATACACTATAATA

AATTGTATGAGAGATAATAATTCAGGATGGAAAGTATCTCTTAATCATAATGAAATAATT

TGGACATTGCAAGATAATGCAGGAATTAATCAAAAATTAGCATTTAACTATGGTAACGCA

AATGGTATTTCTGATTATATAAATAAGTGGATTTTTGTAACTATAACTAATGATAGATTA

GGAGATTCTAAACTTTATATTAATGGAAATTTAATAGATCAAAAATCAATTTTAAATTTA

GGTAATATTCATGTTAGTGACAATATATTATTTAAAATAGTTAATTGTAGTTATACAAGA

TATATTGGTATTAGATATTTTAATATTTTTGATAAAGAATTAGATGAAACAGAAATTCAA
```

```
                               -continued
ACTTTATATAGCAATGAACCTAATACAAATATTTTGAAGGATTTTTGGGGAAATTATTTG

CTTTATGACAAAGAATACTATTTATTAAATGTGTTAAAACCAAATAACTTTATTGATAGG

AGAAAAGATTCTACTTTAAGCATTAATAATATAAGAAGCACTATTCTTTTAGCTAATAGA

TTATATAGTGGAATAAAAGTTAAAATACAAAGAGTTAATAATAGTAGTACTAACGATAAT

CTTGTTAGAAAGAATGATCAGGTATATATTAATTTTGTAGCCAGCAAAACTCACTTATTT

CCATTATATGCTGATACAGCTACCACAAATAAAGAGAAAACAATAAAAATATCATCATCT

GGCAATAGATTTAATCAAGTAGTAGTTATGAATTCAGTAGGAAATAATTGTACAATGAAT

TTTAAAAATAATAATGGAAATAATATTGGGTTGTTAGGTTTCAAGGCAGATACTGTAGTT

GCTAGTACTTGGTATTATACACATATGAGAGATCATACAAACAGCAATGGATGTTTTTGG

AACTTTATTTCTGAAGAACATGGATGGCAAGAAAAATAA
```

LIST OF FIGURES

FIG. 1

Figure 1B:
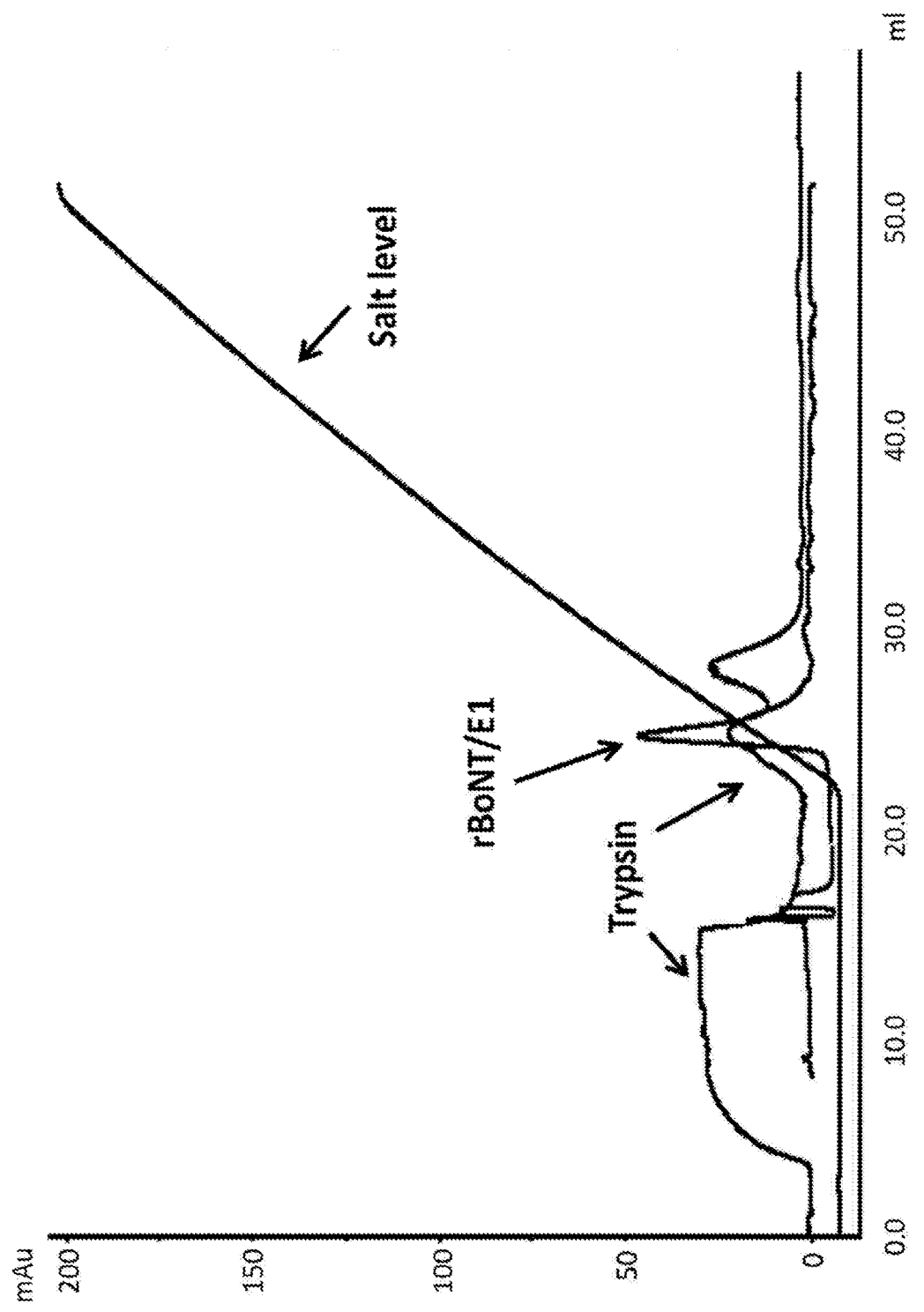

Elution fractions from anion exchange columns on which the separation of trypsin from BoNT/E1 was assessed. The peak of trypsin, BoNT/E1 and the salt gradient are marked. FIG. 1A: Q-Sepharose HP; FIG. 1B: DEAE Sepharose.

FIG. 2

Figure 2B:
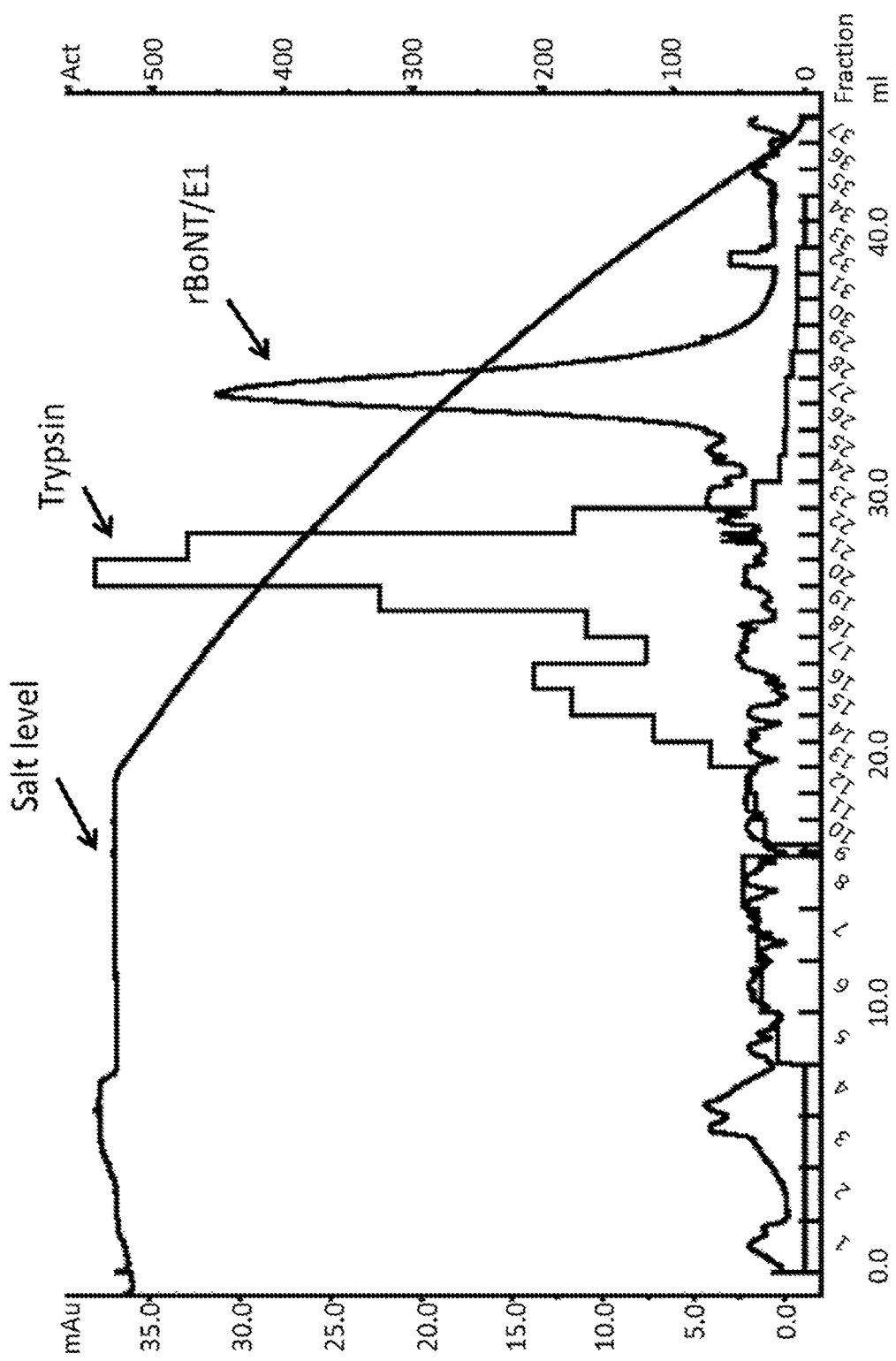
Figure 2C:
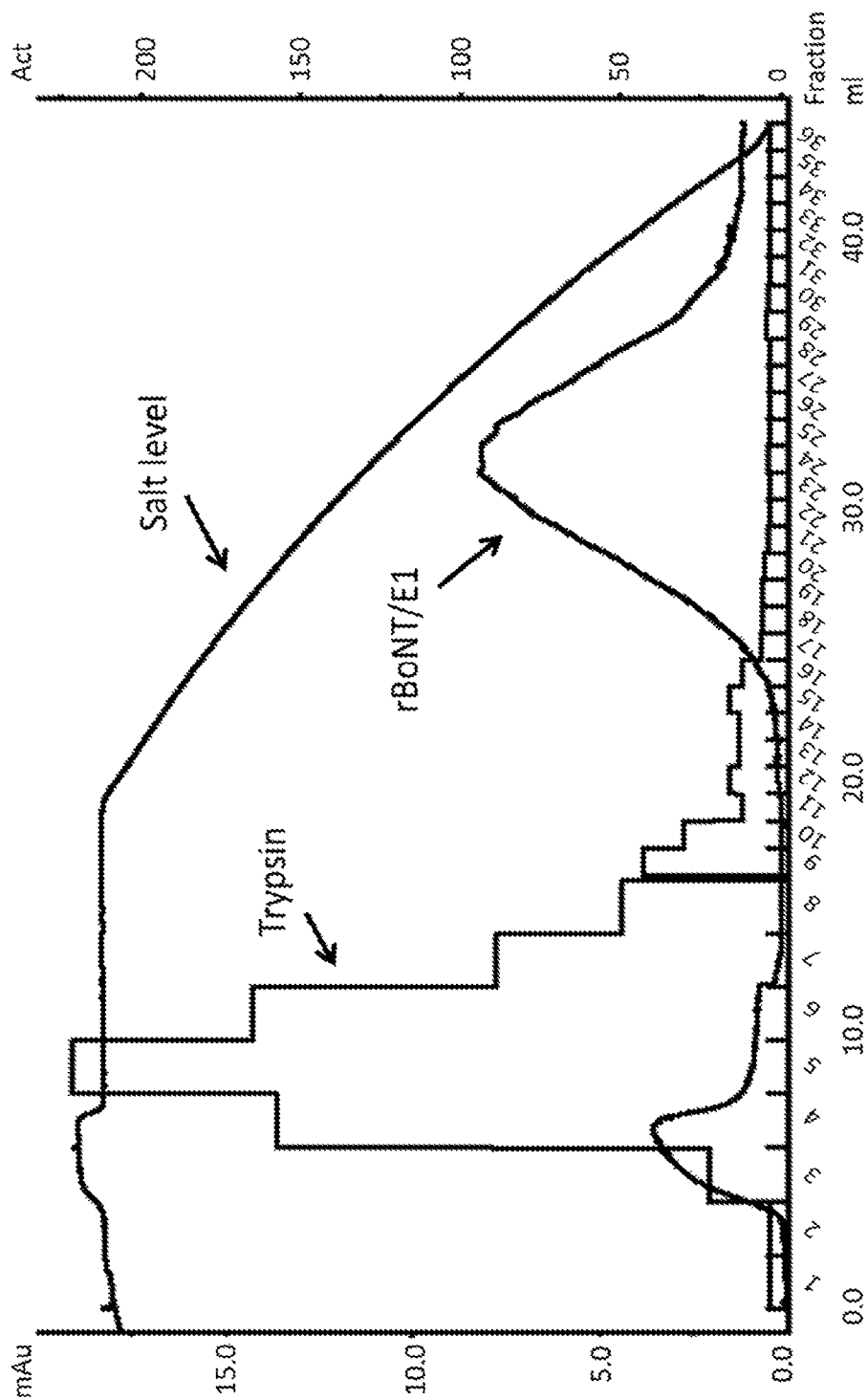

Elution fractions from hydrophobic interaction columns on which the separation of trypsin from BoNT/E1 was assessed. The peak of trypsin, BoNT/E1 and the salt gradient are marked. FIG. 2A: Phenyl Sepharose HP; FIG. 2B: Butyl Sepharose HP; FIG. 2C:) Octyl Sepharose FF.

FIG. 3

Soluble expression level of rBoNT/E1 culture determined by western blotting, compared to commercial BoNT/E1.

FIG. 4

SDS-PAGE of rBoNT/E1 under non-reducing and reducing conditions confirming formation of the di-chain structure.

FIG. 5

The alignment between SEQ ID NOs: 1 and 3.

FIG. 6

The alignment between SEQ ID NO: 1 and the amino acid sequence encoded thereby (SEQ ID NO: 2).

EXAMPLES

Example 1

Construction of an Optimised BoNT/E1 Nucleic Acid Sequence

The DNA sequence was initially designed by back translation of the BoNT/E1 amino acid sequence (SEQ ID NO: 2). A restriction sequence (PstI) was added to the N-terminus and a stop codon and additional restriction sequences, XbaI-Stop codon-HindIII, to the C-terminus. The DNA sequence was then optimised for expression based on the number and location of slow codons (as defined above).

The sequence was optimised to select against slow codons. This was applied particularly at the start of the sequence to get good initiation and start translation. Where slow codons were included (to allow for usage according to expression host codon bias), these were towards the end of the sequence (where the beginning of the sequence is defined as where translation is initiated).

Once the sequence had been designed, the optimised DNA sequence was synthesised in two parts using a unique/native PstI site for later assembly into the full-length toxin gene. The sequence of the first gene included an NdeI site at the amino terminus and a PstI site at the carboxyl terminus. This part of the gene was 2895 bp in length, encoding the BoNT/E1 LC and amino portion of the HC. The sequence of the second gene included a PstI site at the N terminus and HindIII site at the carboxyl terminus, was 882 bp in length and encoded the carboxyl portion of the BoNT/E1 HC.

Example 2

Construction of the Expression Vector BoNT/E1 Nucleic Acid Sequence

An expression vector based on the vector pET-26b(+) (Novagen) was employed, which includes the cloning restriction sites NdeI and HindIII located at the start and end of the DNA encoding the BoNT/E1 ORF. The pET-26b(+) vector was mobilisable-deficient but could be mobilised if co-resident with other mobilisable plasmids. The pET-26b(+) vector was modified to remove mobility genes and render it non-mobilisable.

The expression vector was digested with NdeI and PstI and the purified vector backbone was ligated with the first fragment of BoNT/E1 DNA that had been digested with the same restriction enzymes to create an intermediate product. In the second cloning step, BoNT/E1 DNA from the second fragment that had been digested with PstI and HindIII was ligated into the intermediate product from step one (that had also been digested with the same restriction enzymes). This led to the creation of the final product of BoNT/E1 DNA in the expression vector.

Example 3

Insertion of BoNT/E1 Expression Vector into Host

This example is based on the use of *E. coli* BLR (DE3) cells, though the procedures and methods are equally applicable to any other *E. coli* expression strain. *E. coli* BLR (DE3) competent cells were stored below −70° C. until required. The transformation of the cells was carried out using an adaptation of the manufacturer's protocol. The cells were defrosted on ice and sub aliquots of 10 μL were prepared. An aliquot was transformed using heat shock at 42° C. for 80 seconds with 1 μL of plasmid DNA. After recovering on ice for 5 minutes, 90 μL of animal free SOC broth was added to the transformations which were then transferred to shaking incubators and incubated for 1 hour at 37° C. and 250 rpm. After incubation 90 μL of each transformation was transferred and spread onto animal free LB agar plates supplemented with 50 µg/mL kanamycin. The plates were incubated at 37° C. for 16 hours.

Example 4

Culturing of Host and Expression of Soluble rBoNT/E1 Protein

A single colony of BoNT/E1 transformed in BLR(DE3) cells was used to inoculate a 250 ml conical flask containing 100 ml modified Terrific Broth (mTB) supplemented with 0.2% glucosamine and 30 µg/ml kanamycin. This method would be equally applicable when using a Microbank bead or glycerol stock (10-100 µl) to inoculate the flask.

The flask was incubated for 16 hours at 37° C. with 250 RPM shaking 10 ml of this starter culture was used to inoculate 2 L conical flasks each containing 1 L supplemented with 0.2% glucosamine and 30 µg/ml kanamycin. Cells were grown at 37° C. for ~2 hours at 225 RPM until an $OD_{600}$ of 0.5 was reached. At this point, the culture temperature was dropped to 16° C. After 1 hour, the cells were induced to express BoNT/E1 by addition of 1 mM IPTG for 20 hours. Cells were harvested by centrifugation for 20 min at 4° C., weighed and then stored at −20° C.

Example 5

Extraction of BoNT/E1 Protein from Host and Analysis of Expression Level

Expression cell pastes of rBoNT/E1 were thawed at room temperature and resuspended by pipetting in 3 ml of Tris-NaCL re-suspension buffer per gram of cells supplemented with 10 µl benzonase. Cells were lysed by sonication at a 4 µm amplitude −10×30 s on +>45 s off. The lysate was centrifuged at 4000 g for 1 h at 4° C. to obtain the soluble rBoNT/E1 in the supernatant.

Bradford Assay to Determine Total Protein Concentration of Prepared Lysates

A sample (50 µL) of either diluted rBoNT/E1 lysate or BSA standard was added to 1 mL plastic cuvettes. 450 µL of Coomassie Bradford Assay reagent was added to each cuvette and allowed to incubate at room temperature for 10 minutes before reading $OD_{600}$. The values obtained for the BSA standards were used to determine the amount of protein in the lysate samples.

Preparation of Lysate Samples for Semi-Quantitative Western Blotting Analysis

A commercial sample of BoNT/E1 protein purchased from Metabiologics was used to make up SDS-PAGE standards. SDS-PAGE samples were then prepared from the lysate samples from the expressed cell cultures to a known total protein concentration.

Western Blotting

Figure 3:
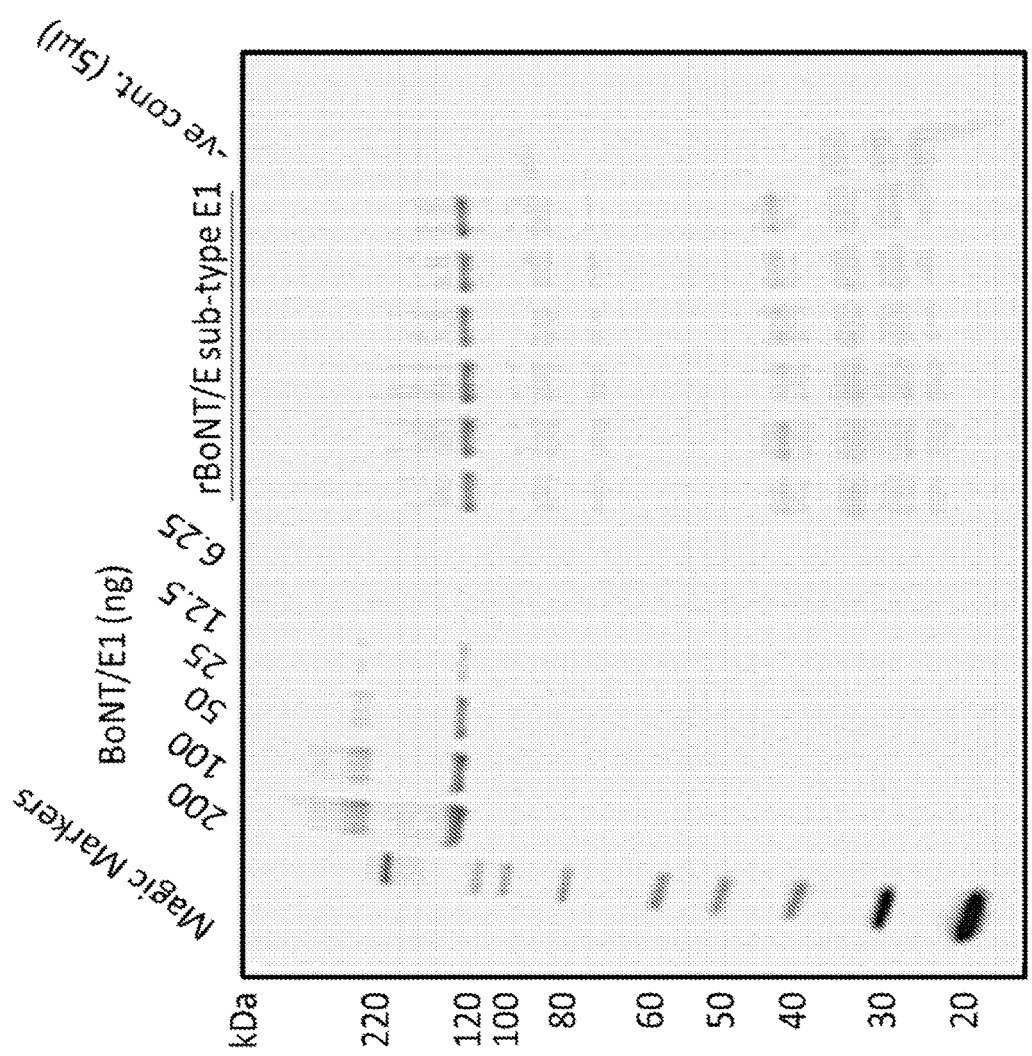

Gels were loaded and ran at 200V for 55 minutes and blotted 0.4 mA for 1 hour onto nitrocellulose membrane in methanol free blotting buffer. The nitrocellulose blots were blocked for 1 hour with 0.5% BSA in PBS-0.1% Tween 20 and then probed with an antibody to BoNT/E1 for 1 hour. The blots were detected with HRP conjugated secondary antibody developed with SuperSignal DuraWest substrate. The developed blots were imaged using a Syngene Imaging Instrument (FIG. 3).

Example 6

Initial Purification and Activation of Target BoNT/E1 Protein to Di-Chain Form

Figure 4:
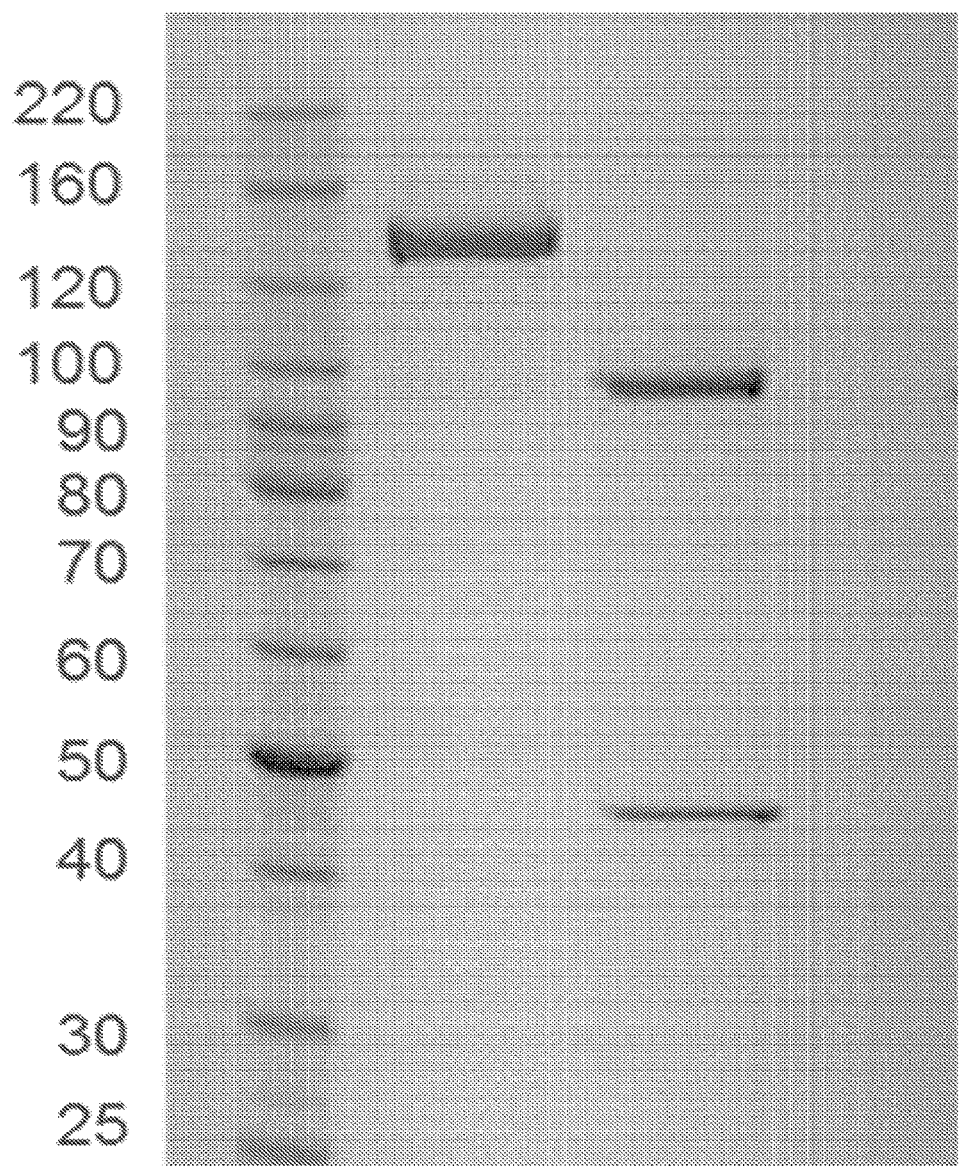

This example was based on one combination of capture and intermediate column steps, though the combination could be altered or reversed to use the same properties in a different order. The clarified supernatant was brought to a high salt concentration and loaded onto a hydrophobic capture column (butyl sepharose). The bound rBoNT/E1 was eluted from the column using a gradient of low salt Tris buffer. The eluted protein was then further purified using an ion-exchange column such as Q-sepharose, eluting a gradient of high salt Tris buffer. Trypsin was then added to the eluted rBoNT/E1 sample to a final concentration of 2.5 µg/ml and incubated at 37° C. for 40 min. This nicked the BoNT/E1 activation loop and formed the final BoNT/E1 di-chain structure, as confirmed by reducing SDS-PAGE (FIG. 4).

Example 7

Final Purification of Target BoNT/E1 Protein Free from Activating Protease

The activated rBoNT/E1 sample was loaded immediately in high salt buffer onto a hydrophobic column (butyl sepharose). The column was washed with high salt buffer to remove the weakly associated trypsin, before a gradient of low salt Tris buffer was applied to further remove the trypsin from the column and the bound rBoNT/E1 protein. The rBoNT/E1 protein was then eluted late in the gradient, away from the trypsin.

Assay to Determine Trypsin Levels

A trypsin ELISA was developed to determine the levels present in the column fractions and in the final BoNT/E1 sample. An anti-trypsin capture antibody was coated to micro-titre plates for 1 hour at 37° C. Trypsin standards and test samples were added onto the plate (100 µL/well) and incubated for 1 h at 37° C. before detection with a second anti-trypsin antibody. The amount of trypsin in each sample/column fraction was then interpolated from the standards and overlaid on the purification chromatogram to confirm the separation of the trypsin from the BoNT/E1 (FIG. 2B).

Example 8

Formulation Comprising Active Di-Chain BoNT/E1 Substantially Free from Trypsin

The following six liquid compositions comprising active di-chain BoNT/E1 were prepared (Table 3).

|  | 1 | 2 | 3 | 4 | 5 | 6 |
| --- | --- | --- | --- | --- | --- | --- |
| Polysorbate 80 | 0.10 mg/mL | 0.10 mg/mL | 0.10 mg/mL | 0.10 mg/mL | — | — |
| Poloxamer | — | — | — | — | 0.04 mg/mL | 0.04 mg/mL |
| Sucrose | 4.0 mg/mL | — | 4.0 mg/mL | — | 4.0 mg/mL | — |
| Mannitol | — | 4.0 mg/mL | — | 4.0 mg/mL | — | 4.0 mg/mL |
| Sodium Chloride | 8.76 mg/mL | 8.76 mg/mL | 8.76 mg/mL | 8.76 mg/mL | 8.76 mg/mL | 8.76 mg/mL |

|   | 1 | 2 | 3 | 4 | 5 | 6 |
|---|---|---|---|---|---|---|
| pH | 6.5 | 6.5 | 6.5 | 6.5 | 6.5 | 6.5 |
| Buffer | L-Histidine/ Hydrochloric acid | L-Histidine/ Hydrochloric acid | Di sodium phosphate/ Citric acid anhydrous | Di sodium phosphate/ Citric acid anhydrous | L-Histidine/ Hydrochloric acid | L-Histidine/ Hydrochloric acid |
| Di-Chain BoNT/E1 | 20 ng/mL | 20 ng/mL | 20 ng/mL | 20 ng/mL | 20 ng/mL | 20 ng/mL |
| MilliQ water | q.s. to 1 mL | q.s. to 1 mL | q.s. to 1 mL | q.s. to 1 mL | q.s. to 1 mL | q.s. to 1 mL |

All six compositions were stored at 25° C. for 12 weeks. The stability of the di-chain BoNT/E1 protease function was assessed during that period using a cell free endopeptidase assay. The monthly degradation rates for the six formulations were below 5% per month over the 12 weeks, which shows the di-chain BoNT/E1 protease function of the six compositions remains stable at 25° C. for at least 12 weeks.

The invention claimed is:

1. A nucleic acid sequence having at least 90% sequence identity to SEQ ID NO: 1, wherein the sequence encodes a single-chain BoNT/E1 polypeptide.

2. The sequence of claim 1, wherein the sequence has a maximum of 160 slow codons.

3. A nucleic acid sequence having at least 90% sequence identity to SEQ ID NO: 1, wherein the sequence encodes a single-chain BoNT/E1 polypeptide comprising an amino acid sequence having at least 95% sequence identity to SEQ ID NO: 2.

4. The sequence of claim 3, wherein the single-chain BoNT/E1 polypeptide comprises one or more of the following amino acids, wherein the amino acid position numbering starts with the N-terminal amino acid residue of the polypeptide and ends with the C-terminal amino acid residue thereof:
   glycine at position 177;
   serine at position 198;
   alanine at position 340;
   leucine at position 773;
   leucine at position 963;
   glutamine at position 964;
   alanine at position 967; and
   asparagine at position 1195.

5. A nucleic acid sequence having at least 90% sequence identity to SEQ ID NO: 1, wherein the sequence encodes a single-chain BoNT/E1 polypeptide and comprises at least 785 synonymous codons when compared to SEQ ID NO: 3.

6. A method for producing a soluble single-chain BoNT/E1 polypeptide, the method comprising expressing the nucleic acid sequence of claim 1 in an *E. coli* expression system.

7. The method of claim 6, wherein the soluble single-chain BoNT/E1 polypeptide is expressed in the cytoplasm of the *E. coli* host cell.

8. The method of claim 6, wherein the soluble single-chain BoNT/E1 polypeptide is expressed at a level of at least 5 mg/L.

9. The method of claim 6, further comprising lysis of the *E. coli* host cell to provide an *E. coli* host cell homogenate containing the soluble single-chain BoNT/E1 polypeptide.

10. A method for producing a soluble di-chain BoNT/E1 protein, the method comprising:
   providing a soluble single-chain BoNT/E1 polypeptide having an amino acid sequence that has at least 95% sequence identity to SEQ ID NO: 2;
   contacting the polypeptide with trypsin in solution, allowing for the trypsin to cleave the single-chain polypeptide, resulting in a di-chain BoNT/E1 protein; and
   separating the soluble BoNT/E1 protein from trypsin by contacting the solution containing soluble BoNT/E1 protein and trypsin with a hydrophobic surface, wherein the soluble BoNT/E1 protein preferentially binds to the hydrophobic surface.

11. The method of claim 10, wherein the polypeptide comprises one or more of the following amino acids, wherein the amino acid position numbering starts with the N-terminal amino acid residue of the polypeptide and ends with the C-terminal amino acid residue thereof:
   glycine at position 177;
   serine at position 198;
   alanine at position 340;
   leucine at position 773;
   leucine at position 963;
   glutamine at position 964;
   alanine at position 967; and
   asparagine at position 1195.

12. The method of claim 10, wherein the soluble single-chain BoNT/E1 polypeptide is provided by expressing a nucleic acid sequence in an *E. coli* expression system, the nucleic acid sequence having at least 90% sequence identity to SEQ ID NO: 1 and encoding a single-chain BoNT/E1 polypeptide.

13. The method of claim 10, wherein the hydrophobic surface is an inert matrix to which a ligand consisting of aryl or alkyl groups is attached.

14. The method of claim 13, wherein the hydrophobic surface comprises butyl ligands, phenyl ligands, and/or octyl ligands.

15. An active di-chain BoNT/E1 protein,
   wherein the first chain comprises an amino acid sequence that has at least 95% sequence identity to the amino acid sequence of positions 1-419 of SEQ ID NO: 2;

wherein the second chain comprises an amino acid sequence that has at least 95% sequence identity to the amino acid sequence of positions 423-1252 of SEQ ID NO: 2; and wherein the first and second chains are joined together by a disulphide bond between cysteine 412 on the first chain and cysteine 426 on the second chain;

wherein the sequences include comprises one or more of the following amino acids, wherein the amino acid position numbering starts with the N-terminal amino acid residue of the polypeptide and ends with the C-terminal amino acid residue thereof:

glycine at position 177;
serine at position 198;
alanine at position 340;
leucine at position 773;
leucine at position 963;
glutamine at position 964;
alanine at position 967; and
asparagine at position 1195.

16. An active di-chain BoNT/E1 protein produced using the method of claim 10.

17. A composition comprising the active di-chain BoNT/E1 protein of claim 15, wherein said composition is substantially free of trypsin.

18. The composition of claim 17, wherein the composition contains less than 10 pg trypsin per 100 ng BoNT/E1 protein.

19. A pharmaceutical composition comprising:
the active di-chain BoNT/E1 protein of claim 15;
a surfactant; and
water;
wherein the composition does not comprise a protein stabilizing agent and is substantially free of trypsin.

20. The pharmaceutical composition of claim 19, further comprising:
sodium chloride;
a buffer to maintain pH between 5.5 and 7.5; and
a disaccharide; and
wherein the water is sterile water.

21. An active di-chain BoNT/E1 protein produced by proteolytic cleavage of the single-chain BoNT/E1 polypeptide produced by the method of claim 6.

* * * * *

```
                         SEQUENCE LISTING

<160> NUMBER OF SEQ ID NOS: 13

<210> SEQ ID NO 1
<211> LENGTH: 3759
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimised BoNT/E1 nucleic acid sequence

<400> SEQUENCE: 1
atgccgaaaa tcaactcttt caactacaac gacccggtta cgaccgtac  catcctgtat      60 atcaaaccgg gtggttgcca ggagttctac aaatctttca acatcatgaa aaacatctgg     120
atcatcccgg aacgtaacgt tatcggtacc accccgcagg acttccaccc gccgacctct     180
ctgaaaaacg gtgactcttc ttactacgac ccgaactacc tccagtctga cgaagaaaaa     240
gaccgtttcc tgaaaatcgt taccaaaatc ttcaaccgta tcaacaacaa cctgtctggt     300
ggtatcctgc tggaagaact gtctaaagct aacccgtacc tgggtaacga caacaccccg     360
gacaaccagt tccacatcgg tgacgcttct gctgttgaaa tcaaattctc taacggttct     420
caggacatcc tgctgccgaa cgttatcatc atgggtgctg aaccggacct gttcgaaacc     480
aactcttcta acatctctct gcgtaacaac tacatgccgt ctaaccacgg tttcggttct     540
atcgctatcg ttaccttctc tccggaatac tctttccgtt tcaacgacaa cagcatgaac     600
gagttcatcc aggacccggc tctgaccctg atgcacgaac tgatccactc tctgcacggt     660
ctgtacggtg ctaaaggtat caccaccaaa tacaccatca cccagaaaca gaaccgctg     720 atcaccaaca tccgtggtac caacatcgaa gagttcctga ccttcggtgg taccgacctg     780
aacatcatca cctctgctca gtctaacgac atctacacca cctgctggc tgactacaaa     840 aaaatcgctt ctaaactgtc taaagttcag gttctaacc cgctgctgaa cccgtacaaa     900 gacgtttcg aagctaaata cggtctggac aaagacgctt ctggtatcta ctctgttaac     960
atcaacaaat tcaacgacat cttcaaaaaa ctgtactctt tcaccgagtt cgacctggcg    1020
accaaattcc aggttaaatg ccgtcagacc tacatcggtc agtacaaata cttcaaactg    1080
tctaacctgc tgaacgactc tatctacaac atctctgaag gttacaacat caacaacctg    1140
```

```
aaagttaact tccgtggtca gaacgctaac ctgaacccgc gtatcatcac cccgatcacc      1200
ggtcgtggtc tggttaaaaa aatcatccgt ttctgcaaga atattgtaag cgttaaagga      1260
ataagaaaaa gtatctgcat cgaaatcaac aacggtgaac tgttcttcgt tgcttctgaa      1320
aactcttaca cgacgacaa catcaacacc ccgaaagaaa tcgacgacac cgttacctct      1380
aacaacaact acgaaaacga cctggaccag gttatcctga acttcaactc tgaatctgct      1440
ccgggtctgt ctgacgaaaa actgaacctg accatccaga cgacgctta catcccgaaa      1500 tacgactcta acggtacctc tgacatcgaa cagcacgacg ttaacgaact gaacgttttc      1560
ttctacctgg acgctcagaa agttccggaa ggtgaaaaca cgttaacct gacctcttct      1620 atcgacaccg ctctgctgga acagccgaaa atctacacct tcttctcttc tgagttcatc      1680
aacaacgtta acaaaccggt tcaggctgct ctgttcgttt cttggattca gcaggttctg      1740
gttgacttca ccaccgaagc taaccagaaa tctaccgttg acaaaatcgc tgacatctct      1800
atcgttgttc cgtacatcgg tctggctctg aacatcggta acgaagctca gaaaggtaac      1860
ttcaaagacg ctctggaact gctgggtgct ggtatcctgc tggagttcga accggaactg      1920
ctgatcccga ccatcctggt tttcaccatc aaatctttcc tgggttcttc tgacaacaaa      1980
aacaaagtta tcaaagctat caacaacgct ctgaaagaac gtgacgaaaa atggaaagaa      2040
gtttactctt tcatcgtttc taactggatg accaaaatca cacccagtt caacaaacgt      2100 aaagaacaga tgtaccaggc tctccagaac caggttaacg ctatcaaaac catcatcgaa      2160
tctaaataca actcttacac cctggaagaa aaaacgaac tgaccaacaa atacgacatc      2220
aaacagatcg aaaacgaact gaaccagaaa gtttctatcg ctatgaacaa catcgaccgt      2280
ttcctgaccg aatcttctat ctcttacctg atgaaactca tcaacgaagt taaaatcaac      2340
aaactgcgtg aatacgacga aaacgttaaa acctacctgc tgaactacat catccagcac      2400
ggttctatcc tgggtgaatc tcagcaggaa ctgaactcta tggttaccga caccctgaac      2460
aactctatcc cgttcaaact gtcttcttac accgacgaca aaatcctgat ctcttacttc      2520
aacaaattct ttaaacgcat taagagttca tcggttctga atatgcggta caaaaatgat      2580
aaatatgtcg atacttctgg atatgatagc aatatcaaca ttaacggcga cgtgtataaa      2640
tatccgacaa ataaaaacca gtttgggata tataacgaca agctgtcgga ggtcaatatt      2700
tctcaaaacg actatatcat ttacgataat aaatataaaa actttagcat tagttttttgg      2760 gttcgtatac ctaattatga caataaaatt gtaaatgtga ataacgagta taccattata      2820
aactgtatgc gcgacaataa cagtggttgg aaggtatcgc tgaaccataa tgagattatc      2880
tggaccctgc aggataatgc aggtataaac cagaaactgg cttttaacta tggaaacgca      2940
aatgggatct cagattacat taataaatgg attttttgtta ccattacgaa cgatcgctta      3000
ggcgactcaa aactttatat taatggcaat ctgatagatc agaaatcaat cttaaatttg      3060
ggcaatattc atgtctctga taacatcttg ttcaagatcg ttaattgcag ttacactcgt      3120
tatattggca ttcgttactt taatatcttc gataagaaac tggacgagac ggaaatccag      3180
actctgtatt caaacgagcc caatactaat atattgaaag attttgggg taactatctt      3240 ttatatgata agaatacta tctccctgaat gtattgaagc caaacaattt catagataga      3300
cgcaaggata gcacattaag tatcaacaat atcagatcta ctatactgtt agcaaatcgc      3360
ctctactccg gtattaaagt gaagattcag cgggttaata actccagtac caatgataat      3420
ctggtccgta agaacgatca ggtatacatc aatttcgtcg cgagcaaaac tcatctcttc      3480
ccgctttacg ccgatacagc tacgacaaac aaggaaaaaa ccataaaaat ttccagctcc      3540
```

```
ggaaacagat tcaatcaagt agttgtaatg aactctgtgg gtaataattg tacgatgaac   3600
tttaagaata acaatgggaa caatattgga cttttgggct tcaaagccga cacagtggtg   3660
gcgtccacct ggtattacac gcacatgcgg gaccatacga attcgaacgg ttgcttctgg   3720
aactttatct cggaagaaca cgggtggcaa gaaaaataa                          3759
```

<210> SEQ ID NO 2
<211> LENGTH: 1252
<212> TYPE: PRT
<213> ORGANISM: Clostridium botulinum

<400> SEQUENCE: 2

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335
```

```
Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750
```

```
Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
        770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                    805                 810                 815

Asp Thr Leu Asn Asn Ser Ile Pro Phe Lys Leu Ser Ser Tyr Thr Asp
                820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                    885                 890                 895

Glu Val Asn Ile Ser Gln Asn Asp Tyr Ile Ile Tyr Asp Asn Lys Tyr
                900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                    965                 970                 975

Tyr Gly Asn Ala Asn Gly Ile Ser Asp Tyr Ile Asn Lys Trp Ile Phe
                980                 985                 990

Val Thr Ile Thr Asn Asp Arg Leu  Gly Asp Ser Lys Leu  Tyr Ile Asn
            995                1000                1005

Gly Asn  Leu Ile Asp Gln Lys  Ser Ile Leu Asn Leu  Gly Asn Ile
1010                1015                1020

His Val  Ser Asp Asn Ile Leu  Phe Lys Ile Val Asn  Cys Ser Tyr
1025                1030                1035

Thr Arg  Tyr Ile Gly Ile Arg  Tyr Phe Asn Ile Phe  Asp Lys Glu
1040                1045                1050

Leu Asp  Glu Thr Glu Ile Gln  Thr Leu Tyr Ser Asn  Glu Pro Asn
1055                1060                1065

Thr Asn  Ile Leu Lys Asp Phe  Trp Gly Asn Tyr Leu  Leu Tyr Asp
1070                1075                1080

Lys Glu  Tyr Tyr Leu Leu Asn  Val Leu Lys Pro Asn  Asn Phe Ile
1085                1090                1095

Asp Arg  Arg Lys Asp Ser Thr  Leu Ser Ile Asn Asn  Ile Arg Ser
1100                1105                1110

Thr Ile  Leu Leu Ala Asn Arg  Leu Tyr Ser Gly Ile  Lys Val Lys
1115                1120                1125

Ile Gln  Arg Val Asn Asn Ser  Ser Thr Asn Asp Asn  Leu Val Arg
1130                1135                1140

Lys Asn  Asp Gln Val Tyr Ile  Asn Phe Val Ala Ser  Lys Thr His
1145                1150                1155

Leu Phe  Pro Leu Tyr Ala Asp  Thr Ala Thr Thr Asn  Lys Glu Lys
```

```
                1160               1165               1170
Thr Ile Lys Ile Ser Ser Ser Gly Asn Arg Phe Asn Gln Val Val
        1175               1180               1185

Val Met Asn Ser Val Gly Asn Asn Cys Thr Met Asn Phe Lys Asn
        1190               1195               1200

Asn Asn Gly Asn Asn Ile Gly Leu Leu Gly Phe Lys Ala Asp Thr
        1205               1210               1215

Val Val Ala Ser Thr Trp Tyr Tyr Thr His Met Arg Asp His Thr
        1220               1225               1230

Asn Ser Asn Gly Cys Phe Trp Asn Phe Ile Ser Glu Glu His Gly
        1235               1240               1245

Trp Gln Glu Lys
        1250

<210> SEQ ID NO 3
<211> LENGTH: 3759
<212> TYPE: DNA
<213> ORGANISM: Clostridium botulinum

<400> SEQUENCE: 3
atgccaaaaa ttaatagttt taattataat gatcctgtta atgatagaac aattttatat      60
attaaaccag gcggttgtca agaattttat aaatcattta atattatgaa aaatatttgg    120
ataattccag agagaaatgt aattggtaca accccccaag attttcatcc gcctacttca    180
ttaaaaaatg gagatagtag ttattatgac cctaattatt tacaaagtga tgaagaaaag    240
gatagatttt aaaaatagt cacaaaaata tttaatagaa taataataa tctttcagga     300 gggattttat tagaagaact gtcaaaagct aatccatatt tagggaatga taatactcca    360
gataatcaat tccatattgg tgatgcatca gcagttgaga ttaaattctc aaatggtagc    420
caagacatac tattacctaa tgttattata atgggagcag agcctgattt atttgaaact    480
aacagttcca atatttctct aagaaataat tatatgccaa gcaatcacgg ttttggatca    540
atagctatag taacattctc acctgaatat tcttttagat ttaatgataa tagtatgaat    600
gaatttattc aagatcctgc tcttacatta atgcatgaat aatacattc attacatgga     660 ctatatgggg ctaaagggat tactacaaag tatactataa cacaaaaaca aaatccccta    720
ataacaaata taagaggtac aaatattgaa gaattcttaa cttttggagg tactgattta    780
aacattatta ctagtgctca gtccaatgat atctatacta atcttctagc tgattataaa    840
aaaatagcgt ctaaacttag caaagtacaa gtatctaatc cactacttaa tccttataaa    900
gatgtttttg aagcaaagta tggattagat aaagatgcta gcggaattta ttcggtaaat    960
ataaacaaat ttaatgatat ttttaaaaaa ttatacagct ttacggaatt tgatttagca   1020
actaaatttc aagttaaatg taggcaaact tatattggac agtataaata cttcaaactt   1080
tcaaacttgt taaatgattc tatttataat atatcagaag gctataatat aaataattta   1140
aaggtaaatt ttagaggaca gaatgcaaat ttaaatccta gaattattac accaattaca   1200
ggtagaggac tagtaaaaaa aatcattaga ttttgtaaaa atattgtttc tgtaaaaggc   1260
ataaggaaat caatatgtat cgaaataaat aatggtgagt tattttttgt ggcttccgag   1320
aatagttata atgatgataa tataaatact cctaaagaaa ttgacgatac agtaacttca   1380
aataataatt atgaaaatga tttagatcag gttatttaa attttaatag tgaatcagca   1440
cctggacttt cagatgaaaa attaaattta actatccaaa atgatgctta taccaaaaa   1500 tatgattcta atggaacaag tgatatagaa caacatgatg ttaatgaact aatgtatttt   1560
```

```
ttctatttag atgcacagaa agtgcccgaa ggtgaaaata atgtcaatct cacctcttca    1620
attgatacag cattattaga acaacctaaa atatatacat ttttttcatc agaatttatt    1680
aataatgtca ataaacctgt gcaagcagca ttatttgtaa gctggataca acaagtgtta    1740
gtagatttta ctactgaagc taaccaaaaa agtactgttg ataaaattgc agatatttct    1800
atagttgttc catatatagg tcttgcttta aatataggaa atgaagcaca aaaaggaaat    1860
tttaaagatg cacttgaatt attaggagca ggtattttat tagaatttga acccgagctt    1920
ttaattccta caattttagt attcacgata aaatctttt taggttcatc tgataataaa     1980
aataaagtta ttaaagcaat aaataatgca ttgaaagaaa gagatgaaaa atggaaagaa    2040
gtatatagtt ttatagtatc gaattggatg actaaaatta atacacaatt aataaaaga    2100 aaagaacaaa tgtatcaagc tttacaaaat caagtaaatg caattaaaac aataatagaa    2160
tctaagtata atagttatac tttagaggaa aaaaatgagc ttacaaataa atatgatatt    2220
aagcaaatag aaaatgaact taatcaaaag gtttctatag caatgaataa tatagacagg    2280
ttcttaactg aaagttctat atcctattta atgaaattaa taaatgaagt aaaaattaat    2340
aaattaagag aatatgatga aatgtcaaa acgtatttat tgaattatat tatacaacat    2400
ggatcaatct tgggagagag tcagcaagaa ctaaattcta tggtaactga taccctaaat    2460
aatagtattc cttttaagct ttcttcttat acagatgata aaattttaat ttcatatttt    2520
aataaattct ttaagagaat taaagtagt tcagttttaa atatgagata taaaaatgat    2580
aaatacgtag atacttcagg atatgattca aatataaata ttaatggaga tgtatataaa    2640
tatccaacta ataaaaatca atttggaata tataatgata aacttagtga agttaatata    2700
tctcaaaatg attacattat atatgataat aaatataaaa attttagtat tagttttggg    2760
gtaagaattc ctaactatga taataagata gtaaatgtta ataatgaata cactataata    2820
aattgtatga gagataataa ttcaggatgg aaagtatctc ttaatcataa tgaaataatt    2880
tggacattgc aagataatgc aggaattaat caaaaattag catttaacta tggtaacgca    2940
aatggtattt ctgattatat aaataagtgg attttttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatattt taatattttt gataaagaat tagatgaaac agaaattcaa    3180
actttatata gcaatgaacc taatacaaat attttgaagg attttttgggg aaattatttg    3240 ctttatgaca aagaatacta tttattaaat gtgttaaaac caaataactt tattgatagg    3300
agaaaagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aattttgtag ccagcaaaac tcacttattt    3480
ccattatatg ctgatacagc taccacaaat aaagagaaaa caataaaaat atcatcatct    3540
ggcaatagat ttaatcaagt agtagttatg aattcagtag gaaataattg tacaatgaat    3600
tttaaaaata ataatggaaa taatattggg ttgttaggtt tcaaggcaga tactgtagtt    3660
gctagtactt ggtattatac acatatgaga gatcatacaa acagcaatgg atgttttgg    3720 aactttattt ctgaagaaca tggatggcaa gaaaaataa                           3759
```

<210> SEQ ID NO 4
<211> LENGTH: 5
<212> TYPE: PRT

```
<213> ORGANISM: Clostridium botulinum

<400> SEQUENCE: 4

Lys Gly Ile Arg Lys
1               5

<210> SEQ ID NO 5
<211> LENGTH: 7
<212> TYPE: PRT
<213> ORGANISM: Clostridium botulinum

<400> SEQUENCE: 5

Val Lys Gly Ile Arg Lys Ser
1               5

<210> SEQ ID NO 6
<211> LENGTH: 9
<212> TYPE: PRT
<213> ORGANISM: Clostridium botulinum

<400> SEQUENCE: 6

Ser Val Lys Gly Ile Arg Lys Ser Ile
1               5

<210> SEQ ID NO 7
<211> LENGTH: 10
<212> TYPE: PRT
<213> ORGANISM: Clostridium botulinum

<400> SEQUENCE: 7

Val Ser Val Lys Gly Ile Arg Lys Ser Ile
1               5                   10

<210> SEQ ID NO 8
<211> LENGTH: 11
<212> TYPE: PRT
<213> ORGANISM: Clostridium botulinum

<400> SEQUENCE: 8

Ile Val Ser Val Lys Gly Ile Arg Lys Ser Ile
1               5                   10

<210> SEQ ID NO 9
<211> LENGTH: 12
<212> TYPE: PRT
<213> ORGANISM: Clostridium botulinum

<400> SEQUENCE: 9

Asn Ile Val Ser Val Lys Gly Ile Arg Lys Ser Ile
1               5                   10

<210> SEQ ID NO 10
<211> LENGTH: 13
<212> TYPE: PRT
<213> ORGANISM: Clostridium botulinum

<400> SEQUENCE: 10

Lys Asn Ile Val Ser Val Lys Gly Ile Arg Lys Ser Ile
1               5                   10

<210> SEQ ID NO 11
<211> LENGTH: 14
<212> TYPE: PRT
<213> ORGANISM: Clostridium botulinum
```

```
<400> SEQUENCE: 11

Cys Lys Asn Ile Val Ser Val Lys Gly Ile Arg Lys Ser Ile
1               5                   10

<210> SEQ ID NO 12
<211> LENGTH: 14
<212> TYPE: PRT
<213> ORGANISM: Clostridium botulinum

<400> SEQUENCE: 12

Lys Asn Ile Val Ser Val Lys Gly Ile Arg Lys Ser Ile Cys
1               5                   10

<210> SEQ ID NO 13
<211> LENGTH: 15
<212> TYPE: PRT
<213> ORGANISM: Clostridium botulinum

<400> SEQUENCE: 13

Cys Lys Asn Ile Val Ser Val Lys Gly Ile Arg Lys Ser Ile Cys
1               5                   10                  15
```